US006673347B1

(12) United States Patent
Offord et al.

(10) Patent No.: US 6,673,347 B1
(45) Date of Patent: *Jan. 6, 2004

(54) POLYPEPTIDE AND PROTEIN DERIVATIVES AND PROCESS FOR THEIR PREPARATION

(75) Inventors: Robin Ewart Offord, Collex Bossy (CH); Keith Rose, Geneva (CH)

(73) Assignee: Gryphon Therapeutics, South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/241,687

(22) Filed: May 12, 1994

Related U.S. Application Data

(63) Continuation of application No. 08/089,051, filed on Aug. 6, 1993, now abandoned, which is a continuation of application No. 07/866,262, filed on Apr. 10, 1992, now abandoned, which is a continuation of application No. 07/742,159, filed on Aug. 1, 1991, now abandoned, which is a continuation of application No. 07/506,545, filed on Apr. 5, 1990, now abandoned, which is a continuation of application No. 07/380,738, filed on Jul. 17, 1989, now abandoned, which is a continuation of application No. 07/220,196, filed on Jul. 18, 1988, now abandoned, which is a continuation of application No. 07/043,530, filed on Apr. 28, 1987, now abandoned.

(30) Foreign Application Priority Data

Apr. 30, 1986 (GB) .............................. 8610551

(51) Int. Cl.[7] ........................ A61K 39/395; C07K 1/00; C07K 16/00
(52) U.S. Cl. ................ 424/178.1; 424/179.1; 530/402; 530/403; 530/406; 530/410; 530/387.1
(58) Field of Search ................ 530/402, 403, 530/406, 410, 387.1; 424/178.1, 179.1

(56) References Cited

U.S. PATENT DOCUMENTS

| | | | |
|---|---|---|---|
| 3,856,771 A | | 12/1974 | Jackson |
| 3,864,325 A | | 2/1975 | Smyth |
| 3,903,069 A | | 9/1975 | Gregory et al. |
| 4,029,642 A | | 6/1977 | Obermeier |
| 4,183,849 A | | 1/1980 | Hansen et al. |
| 4,352,751 A | * | 10/1982 | Wieder et al. ............... 530/391 |
| 4,496,722 A | * | 1/1985 | Gallop et al. .................. 544/69 |
| 4,668,503 A | * | 5/1987 | Hnatowich .................... 424/85 |
| 4,691,006 A | * | 9/1987 | Stevens ....................... 530/324 |
| 4,699,784 A | | 10/1987 | Shih et al. |
| 4,707,352 A | * | 11/1987 | Starianopoulos ............. 424/85 |
| 4,722,899 A | * | 2/1988 | Hamaoka et al. ......... 435/172.2 |
| 5,045,451 A | * | 9/1991 | Uhr et al. .................. 435/7.23 |
| 5,106,951 A | * | 4/1992 | Morgan et al. .......... 530/391.9 |
| 6,001,364 A | * | 12/1999 | Rose et al. ............... 424/193.1 |
| 6,174,530 B1 | * | 1/2001 | Rose et al. ............... 424/193.1 |
| 6,217,873 B1 | * | 4/2001 | Rose et al. ............... 424/193.1 |

FOREIGN PATENT DOCUMENTS

| | | |
|---|---|---|
| JP | 3525/72 | 2/1972 |
| JP | 56145222 | * 11/1981 |

OTHER PUBLICATIONS

Hermentin et al., Behring Inst. Mitt, No. 82, pp. 197–215 (1988).*
Seaver, Genetic Engineering News, pp. 10 and 21, (1994).*
Waldmann, Science, vol. 252, pp. 1657–1661 (1991).*
Hardman et al, Biochem.Soc. Trans.(1983), 11(2), 182, (abstract).*
Bierman et al , ARch. Lebensmittelhyg. 31(2), 51–7, 1980.*
Bayer et al., The Avidin–Biotin Complex in Affinity Cytochemistry, Methods in Enzymology 62:308 (1979).
Brady et al., Selective Decrease in $T_1$ Relaxation Times . . . , abstract, Magnetic Resonance in Medicine 1:286 (1984).
Canova–Davis et al., Semisynthesis of Insulin:Specific Activation of the Arginine Carboxyl Group . . . , Biochemistry 20:7053 (1981).
Chua et al., Attachment of Immunoglobulin to Liposomal Membrane Via Protein Carbohydrate, Biochim. Biophys. Acta 800:291 (1984).
Dixon et al., Specific Modification of $NH_2$–Terminal Residues by Transamination, Methods in Enzymology 25:409 (1979).
Fields et al., A Spectrophotometric Method for the Microdetermination of Periodate, Biochem J. 108:883 (1968).
Friedman et al., Reductive Alkylation of Proteins With Aromatic Aldehydes and Sodium Cyanoborohydride, Int. J. Peptide Protein Res. 6:183 (1974).
Gray, The Direct Coupling of Oligosaccharides to Proteins and Derivatized Gels, Arch. Biochem. Biophys. 163:426 (1974).
Hansske et al., Modification of the 3' Terminus by Periodate Oxidation, Methods in Enzymology LIX:172 (1979).
Hnatowich et al., Radioactive Labeling of Antibody: A Simple And Efficient Method, Science 220:613 (1983).
Heitzmann et al., Use of the Avidin–Biotin Complex for Specific Staining of Biological Membranes . . . , Proc. Natl. Acad. Sci. USA 71:3537 (1974).

(List continued on next page.)

Primary Examiner—Padmashri Ponnaluri
(74) Attorney, Agent, or Firm—Jeffrey I. Auerbach; Liniak, Berenato & White

(57) ABSTRACT

Protein and polypeptide derivatives and their salts are claimed characterized in that a protein or polypeptide is conjugated via an intermediate grouping containing at least one radical of the formula —C(R)═N— (or —N═C(R)—) or —CH(R)—NH— (or —NH—CH(R)—), wherein R is hydrogen or a hydrocarbon residue which may be substituted, with the same or a different protein or polypeptide, with a reporter group or a cytotoxic agent as well as a process for their preparation and the novel intermediates therefor.

69 Claims, No Drawings

OTHER PUBLICATIONS

Hofmann et al., Avidin Binding of Carboxyl–Substituted Biotin and Analogues, Biochemistry 21:978 (1982).

Itaya et al., Cell Surface Labeling of Erythrocyte Glycoproteins . . . , Biochem. Biophys. Res. Commun. 64:1028 (1975).

Jentoft et al., Protein Labeling by Reductive Alkylation, Methods in Enzymology 91:570 (1983).

Ji, Bifuctional Reagents, Methods in Enzymology 91:580 (1983).

Jones et al., The Proteinase–catalysed Synthesis of Peptide Hydrazides, Biochem. J 203:125 (1982).

King et al., Preparation of Protein Conjugates Via Intermolecular Hydrazone Linkage, Biochemistry 25:5774 (1986).

Kraehenbuhl et al., Preparation and Characterization of an Immuno–Electron Microscope Tracer, J. Exp. Med. 139:208 (1974).

Krejcarek et al., Covalent Attachment of Chelating Groups to Macromolecules, Biochem. Biophys. Res. Commun. 77:581 (1977).

Mach et al., Tumor Localization in Patients by Radiolabeled Monoclonal Antibodies . . . , Cancer Res. 43:5593 (1983).

Murayama et al., Modification of Immunoglobulin G Using Specific Reactivity of Sugar Moiety, Immunochem. 15:523 (1978).

Quash et al., The Preparation of Latex Particules with Covalently Bound Polyamines . . . , J. Immunol. Methods 22:165 (1978).

Rodwell et al., Site–specific Covalent Modification of Monoclonal Antibodies . . . Proc. Natl. Acad. Sci. USA 83:2632 (1986).

\* cited by examiner

POLYPEPTIDE AND PROTEIN DERIVATIVES AND PROCESS FOR THEIR PREPARATION

CROSS REFERENCE TO RELATED APPLICATIONS

This application is a continuation of U.S. application Ser. No. 08/089,051, filed Aug. 6, 1993, now abandoned, which is a continuation of application Ser. No. 07/866,262, filed Apr. 10, 1992, now abandoned, which is a continuation of application Ser. No. 07/742,159, filed Aug. 1, 1991, now abandoned, which is a continuation of application Ser. No. 07/506,545, filed Apr. 5, 1990, now abandoned, which is a continuation of application Ser. No. 07/380,738, filed Jul. 17, 1989, now abandoned, which is a continuation of application Ser. No. 07/220,196, filed Jul. 18, 1988, now abandoned, which is a continuation of application Ser. No. 07/043,530, filed Apr. 28, 1987, now abandoned.

TECHNICAL FIELD

This invention relates to novel polypeptide and protein derivatives in which polypeptides and proteins are conjugated by bridging molecules to the same kind of polypeptides or proteins, other kinds of proteins or polypeptides, reporter groups or cytotoxic agents.

BACKGROUND OF THE INVENTION

In the diagnosis of many forms of disease, as well as when following the effects of treatment, it would often be desirable to use labelled proteins that bind to specific target structures in the body. For example, when diagnosing or treating cancer, it would be desirable to be able to detect both primary tumours and metastases using labelled tumour-specific antibodies. Many reports have appeared on the labelling of proteins and antibodies by random chemical attack on their side chains. In such a process, most frequently, the side chains of the tyrosines are iodinated (Mach et al., Cancer Research 43, 5593–5600 [1983]), or the side-chains of the lysines are acylated. In this latter case the acylation is often by groups that chelate metals (e.g. Hnatowich et al., Science 220, 613–615 [1983]). Subsequently, the chelating groups can be used to bind radioactive metals. It has also been suggested but not yet been satisfactorily tested to bind to such molecules paramagnetic ions for nuclear magnetic resonance (NMR) imaging (Brady et al., Magnetic Resonance in Medicine 1, 286 [1984]). The labelling of proteins, especially of antibodies, however, has so far always been effected in a more or less random way.

Random substitutions on biological active proteins, for example random substitutions on antibody molecules, can have a number of drawbacks:

1. If by chance a particularly reactive site were to lie in the active site of the protein a substitution at this site would possibly inactivate the protein, e.g. a particularly valuable monoclonal antibody might be rendered totally useless if by chance a side chain particularly reactive towards substitution were to lie in the antigen-binding site. The substitution would then inactivate the antibody.
2. Even when the active site of the protein (e.g. an antibody) escapes serious damage, a high number of substitutions on the protein—which may be desirable, e.g. in order to have a high intensity in case of radioactive labelling via chelating groups—might change its physico-chemical properties (e.g. solubility).
3. A random, multiple substituted product constitutes a heterogenous mixture of molecules with different properties, with attendant problems of assuring constant properties from batch to batch.

SUMMARY OF THE INVENTION

The present invention relates to novel polypeptide and protein derivatives, to a process for their preparation, to their use and to novel intermediates therefor. The novel polypeptides and proteins of the present invention are, more specifically, polypeptides and proteins which are conjugated via an intermediate grouping containing at least one radical of the formula —C(R)=N— (or —N=C(R)—) or —CH(R)—NH— (or —NH—CH(R)—), wherein R is hydrogen, an aliphatic, cycloaliphatic, aromatic or araliphatic hydrocarbon group which group may be substituted, with themselves or each other, with a different polypeptide or protein or with a reporter group or a cytotoxic agent. These compounds are obtained by condensation of two reactants one of which is an aldehyde (or acetalized aldehyde) or ketone the other being an amino compound thus yielding a Schiff base or azomethine type compound which, if desired or necessary, can be stabilized in a further reaction, viz. by reduction of the —C(R)=N— (or —N=C(R)—) radical to a —CH(R)—NH— (or —NH—CH(R)—) radical.

DESCRIPTION OF THE INVENTION

The present invention in a major aspect makes use of the fact that enzymes can direct bifunctional reagents with suitable reactive groups at specific sites in polypeptides or proteins (e.g. antibodies). These sites are preferably the carboxyl terminus of the polypeptide chain, which is at least in terms of primary structure in most cases far from the active site of proteins. This is especially true for antibody molecules where the carboxyl terminus is furthest away from the antigen-binding site. Therefore problem No. 1 mentioned above can be eliminated by the process of the present invention. The limitation of the substitution to a specific site such as the carboxyl terminus, will also eliminate problems No. 2 and No. 3, above.

However, in a further aspect the present invention makes use of the fact that specific bifunctional reagents with suitable reactive groups preferably or specifically react at non carboxy terminus sites of the molecule, viz. with specific side chains or the amino terminal amino group in a non-enzymatic reaction.

Examples of bifunctional reagents with suitable reactive groups are compounds with an amino group at one end and with a formyl or amino group (preferably in protected form) at the other end, such as o-, m- or p-formylphenylalanine.

Therefore, the polypeptide and protein derivatives of the present invention can be prepared by a condensation reaction between an aldehyde or ketone and an amino compound to yield the desired derivative of the azomethine or Schiff base type and, if desired, subsequent reduction of the —C=N— radical (which is relatively labile in case one of the reaction partners is an amine and the product is a Schiff base) to form a corresponding derivative containing a —CH$_2$—NH— radical. The amino compound can be an amine, an O-alkylated hydroxylamine or a hydrazide. In the case of an O-alkylated hydroxylamine reacting with a carbonyl compound (aldehyde or ketone) oximes are obtained containing a —C(R)=N—O— radical. Since such compounds are relatively stable no subsequent reduction, albeit possible, is necessary to form a corresponding derivative containing a —CH(R)—NH—O— radical. In the case of a hydrazide reacting with a carbonyl compound the reaction product will contain a —C(R)=N—NH— radical which again is relatively stable and needs no reduction to form a corresponding derivative containing a —CH(R)—NH—NH— radical.

The basic reaction scheme of which the present makes use is >C=O+H$_2$N—→>C=N—→>CH—NH—. In this scheme, one complementary group (carbonyl or amino) is placed at the N- or C-terminus of a protein or polypeptide under mild conditions. To obtain specificity (discrimination between an attached amino group and lysine side chains of the protein or polypeptide) a reactive amino group attached to a protein must be an aromatic one, i.e. must be directly attached to an aromatic group, such as phenyl or it must be directly attached to —O— or to —NH—CO—, i.e. be an O-alkyl-hydroxylamine or a hydrazide, respectively.

If at least one of the reactive groups (carbonyl or amino group) of the reaction partners is aromatic, preferably if both are aromatic, it was found that the condensation reaction is rapid, and highly efficient even at surprisingly low concentrations of reactants. The reactivities involved are sufficiently great to permit the attachment of, e.g. a polymeric chelating group to the specific site, which means that at the cost of a single modification at a specific site on the protein known to be safe for this purpose, it is possible to introduce virtually as many of the desired substituent groups as required for high radioactivity. This feature again permits to overcome problem No. 2, addressed above, since a high number of substitutions spread over the whole protein in order to achieve a high enough intensity of labelling is no longer required.

For the reasons discussed above, it is usually preferable to have the group which is to participate in the condensation reaction to form a Schiff base type compound attached specifically, via enzymatic methods, to the carboxy terminus of the protein or polypeptide.

Under certain circumstances, however, it may be satisfactory and convenient to form Schiff base links via groups introduced elsewhere and groups introduced by other methods. Usually, but not always, such methods are less specific than the carboxy-terminal enzymatic method. Circumstances under which these other methods might be employed are:

(i) in cases where the carboxy-terminal region is important for function or should not be altered for other reasons and (ii) where particular properties of the protein or polypeptide, e.g. its possessing a single or rather few side chain residues of an amino acid for which specific chemical modification reagents exist or may be designed, can usefully be exploited.

Therefore, it is possible to combine group-specific chemical modification of protein or polypeptide side chains with subsequent coupling to Schiff bases. In the context of the present specification and claims the term "Schiff base" is meant to extend to all protein or polypeptide derivatives exhibiting a >C=N— radical and thus also encompasses compounds, such as, oximes or hydrazones. A wide variety of group-specific protein modification reagents are known which permit the modification, with various degrees of specificity, of the functional groups present in proteins. Furthermore, many examples exist where two of the chemically reactive groups present in such reagents have been incorporated into a single molecule to provide a bivalent reagent (see e.g. the Catalogue of the Pierce Chemical Co., the world's leading manufacturer of protein cross-linking reagents). So far, none of these reagents have been used for Schiff base chemistry. It should be noted that great advantage is to be made from combining, in the same molecule, a group capable of reacting with functional groups of proteins or polypeptides and a group capable (after deprotection, if it is used in protected form) of forming a Schiff base link with a complementary group on another molecule, viz. a carbonyl or amino group. Such reagents are represented by the general formula $R^3$—X—$R^1$, where $R^3$ is a chemical group which reacts with functional groups of proteins or polypeptides, X is a bivalent organic group or may be absent but is preferably an aromatic radical directly adjacent to $R^1$ and must be an aromatic group or oxygen directly adjacent to $R^1$ where $R^1$ is amino or protected amino and $R^1$ is carbonyl, acetalised formyl (e.g. dimethoxy or diethoxy methyl), amino or protected amino. Suitable amino protecting groups are those which are stable enough to withstand the attachment of $R^3$ to the polypeptide or protein, yet labile enough to be removed under conditions which do not irreversibly denature the polypeptide or protein. Many such groups are known to the art, e.g., citraconyl, trifluoroacetyl, Boc, BPOC, MSC. Suitable groups for $R^3$ are well known to the art (c.f., for example, Means, G. E. and Feeney, R. E. [1971] "Chemical Modification of Proteins", Holden-Day, San Francisco): groups that react selectively with amino-groups are, e.g., active-esters such as hydroxysuccinimide esters, o-nitrophenyl esters, imidates or haloaromatics with a nucleus activated to nucleophilic substitution; groups that react selectively with sulphhydryl-groups are, e.g., haloalkyls, activated disulphides, aziridines, activated vinyl compounds; groups that react selectively with guanido-groups are, e.g., alpha- or beta-dicarbonyls; aromatic-group selective reagents are, e.g., diazonium compounds; indole-group selective compounds are, e.g., aromatic sulphenyl halides, and carboxyl-group selective reagents are, e.g., diazoalkanes and amino compounds in the presence of condensing reagents such as DCCI.

The polypeptide and protein derivatives of the present invention can be represented by the formula

A—X—Z—X'—B    (I)

wherein

A is the residue of a protein or polypeptide;

B is the residue of a protein or polypeptide, of a reporter group or of a cytotoxic agent;

X and X' independently from each other are bivalent organic radicals or may be absent;

Z is a bivalent radical selected from the group consisting of —C(R)=N—, —N=C(R)—, —CH(R)—NH—, —NH—CH(R)—, —C(R)=N—Y—N=C(R)—, —N=C(R)—Y—C(R)=N—, —CH(R)—NH—Y—NH—CH(R)— or —NH—CH(R)—Y—CH(R)—NH—, wherein R is hydrogen, an aliphatic, cycloaliphatic, aromatic or araliphatic hydrocarbon group, which group may be substituted with the same or a different protein or polypeptide, a reporter group or a cytotoxic agent, with at least one aromatic radical or oxygen adjacent to nitrogen and Y is a bivalent organic group and salts thereof.

The invention also extends to salts of the protein and polypeptide derivatives mentioned above, especially to metal salts thereof. Of most interest among the salts are the metal chelate complexes useful for in vivo imaging.

Thus, the compounds of formula I are derivatives of (or modified) polypeptides or proteins. Typical polypeptides and proteins, the residues of which are designated A and B in formula I, are on the one hand those occurring in nature and capable of being isolated from nature independent from whether their structure and/or amino acid sequences and glycosylation pattern has already been identified or not and on the other hand those which have been or can be prepared synthetically or semisynthetically in accordance with methods well-known in the art. Preferred compounds of formula I are derivatives of polypeptides and proteins of medical interest, among which, e.g., derivatives of immunoglobulins, especially antibodies of the IgG type. It will be appreciated that not only complete antibodies can be labelled or derivatised using the method of the present invention but also subunits thereof which are still functional, such as F(ab')$_2$ or Fab fragments.

Formula I comprises compounds of the following types:

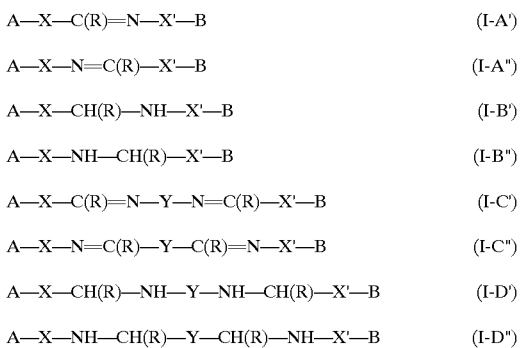

wherein A, B, X, X', R and Y are as defined above.

With R=hydrogen (i.e. with one of the reaction partners being an aldehyde or a protected aldehyde) compounds of the following general formulae are obtained:

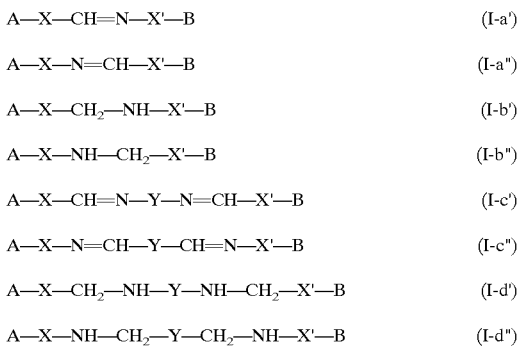

wherein A, B, X, X' and Y are as defined above.

In the case where B represents a protein or polypeptide residue these residues may be different from or identical with A. In the first case hetero-dimers of proteins and polypeptides and in the second case homo-dimers of proteins and polypeptides can be obtained.

B may alternatively represent the residue of a cytotoxic agent or a reporter group. Cytotoxic agents in the present context are defined to comprise all compounds generally summarized under this expression such as cytostatics and toxins. Cytostatics of specific interest are those chemotherapeutically active compounds against cancer, i.e. cancerostatics (carcinostatics). The term "reporter group" is meant to define compounds which are easily detectable by analytical means in vitro and/or in vivo and which confer this property to compounds to which they are bound. This term comprises, e.g., any organic compounds/groups which are capable of binding strongly to metals (including and preferably radioactive metals). Especially preferred among such reporter groups are metal chelating agents/groups (chelons), e.g., desferrioxamine or DTPA (systematic names see below). Apart from being a compound/group capable of being radioactively labelled, reporter groups may be fluorescent groups or groups capable of being monitored by NMR or ESR spectroscopy.

The groups X and X' can be absent or represent bivalent radicals of aliphatic, aromatic or araliphatic compounds and can be substituted. X and X' may be identical or can differ from each other, e.g., only one may be present. Preferred groups X and X' are aromatic radicals, e.g., —NH—C$_6$H$_4$— or araliphatic radicals, e.g., —NH—CH$_2$—CH$_2$—C$_6$H$_4$—, —NH—CH(COOCH$_3$)—CH$_2$—C$_6$H$_4$— or —NH—CH(CONH$_2$)—CH$_2$—C$_6$H$_4$—, since the forming of the Schiff base type compounds is favoured in this case. Examples of aliphatic groups X or X' are —O—CH$_2$—CO—, —NH—CH$_2$—CO—, —NH—CH$_2$—CH$_2$—S—CH$_2$—. It is essential that in case there are aliphatic amino groups present in the protein or polypeptide molecule (which latter case generally happens, e.g., if lysine is present) that the aromatic group is adjacent to the N-atom of group Z of formula —N=CH— or —NH—CH$_2$—, which means that the Schiff base formation occurs via an aromatic amino group at the side of the protein or polypeptide. In case the protein, polypeptide or the cytotoxic agent or reporter group contains already such an aromatic amino group through which the coupling can be effected X and/or X' will be absent. In this case the N-atom of Z originates from the starting protein, polypeptide, cytotoxic agent or the reporter compound. The same applies with respect to an aromatic formyl function.

In order to reach highest specificity in the coupling reaction it is preferred either to use aromatic aldehydes and aromatic amino compounds so that in the Schiff base compounds obtained the radicals adjacent to both the N- and the C-atom of the —CH=N— or —N=CH— group are aromatic groups, preferably phenylene groups, or to use ketones and O-alkylhydroxylamines.

In case one of the reaction partners is a ketone it is preferable to use amino compounds which are stronger nucleophiles than arylamino compounds and which are known to react rapidly, specifically and under mild conditions with carbonyl groups. Such amino compounds include substituted hydrazines (hydrazides) and O-substituted, preferably O-alkylated, hydroxylamines, such as H$_2$N—O—CH$_2$—COOH. The stability at non-extreme pH of hydrazones and oximes means that the reduction step >C=N—X→>CH—NH—X, which is required when X is aryl, is not necessary, albeit possible. In the case of a hydroxylamino compound being used as nucleophile compound of formula I will be obtained wherein Z is a bivalent radical selected from the group consisting of —CH=N—O—, —O—N=C(R)—, —CH(R)—NH—O—, —O—NH—CH(R)—, —C(R)=N—O—Y—O—N=C(R)—, —O—N=C(R)—Y—C(R)=N—O—, —CH(R)—NH—O—Y—O—NH—CH(R)— and —O—NH—CH(R)—Y—CH(R)—NH—O—, with R and Y being as defined above.

Compounds of formulae I-C', I-C", I-D' and I-D" are obtained when a diamino compound of formula H$_2$N—Y—NH$_2$ or a dicarbonyl compound of formula OC(R)—Y—C(R)O is reacted with a carbonyl or an amino compound respectively. Y can be any bivalent organic group, i.e. an aliphatic, aromatic or araliphatic group. For obvious reasons simple molecules are preferred. A most preferred aromatic Y group is phenylene while in case of an aliphatic Y group this group has two O- or NH-radicals. It is also evident that although compounds of formulae I-C', I-C", I-D' and I-D" can be prepared using methods well-known in the art wherein A and B and/or X and X' are different, the preferred compounds of that type are those wherein B is identical with A and X' is identical with X (including the possibility that both latter groups are absent). Thus symmetric proteins or polypeptide dimers are obtainable which are coupled almost specifically via a —C—N—Y—N—C— or a —N—C—Y—C—N— chain.

The compounds of formula I and their salts in accordance with the process of the present invention are obtained by condensing a compound of formula $$A-X-R^1 \tag{II}$$

wherein $R^1$ is —CO—R, acetalized formyl or amino and

A is a residue of a protein of polypeptide, X is a bivalent organic radical or may be absent, and R is hydrogen or an aliphatic, cycloaliphatic, aromatic or araliphatic hydrocarbon group, which group may be substituted with the same or a different protein or polypeptide, a reporter group or a cytotoxic agent, with a compound of formula $$R^2-X'-B \tag{III}$$

wherein $R^2$ is amino in case $R^1$ in the compound II above is —CO—R or acetalized formyl and is —CO—R or acetalized formyl in case $R^1$ in compound II above is amino and X' is a bivalent organic radical or may be absent, B is a residue of a protein or polypeptide, a reporter group or a cytotoxic agent, and R is hydrogen or an aliphatic, cycloaliphatic, aromatic or araliphatic hydrocarbon group, which group may be substituted with the same or a different protein or polypeptide, a reporter group or a cytotoxic agent, or condensing a compound of formula II above with a compound of formula $$R^2-Y-R^2 \tag{IV}$$

wherein

Y is as defined above and $R^2$ is amino in case $R^1$ in the compound II above is —CO—R or acetalized formyl and is —CO—R or acetalized formyl in case $R^1$ in compound II above is amino to form a Schiff base and, if desired, reducing the —C(R)=N— or —N=C(R)-radical(s) generated by the condensation to —CH(R)—NH— or —NH—CH(R)-radical(s) respectively and, if desired, forming a salt.

Thus either a carbonyl compound A—X—C(R)O, in case of R=H an aldehyde or an acetal thereof, preferably the methyl or ethyl acetal, is reacted with an amino compound, preferably an aromatic amine $H_2N$—X'—B or an O-derivative of hydroxylamine, or an amino compound, preferably an aromatic amine A—X—$NH_2$ or an O-derivative of hydroxylamine, is reacted with a carbonyl compound O(R)C—X'—B, in case of R=H an aldehyde or a corresponding acetal, preferably the methyl or ethyl acetal, to form the Schiff base.

If symmetric bisproteins or bispolypeptides are desired a carbonyl compound A—X—C(R)O or an acetal thereof, in case R=H, is reacted with a diamino compound $H_2N$—Y—$NH_2$, or an amino compound A—X—$NH_2$, preferably an aromatic amino compound or an O-derivative of hydroxylamine, is reacted with a carbonyl compound O(R)C—Y—C(R)O or an acetal thereof, in case R=H.

As follows from the definitions of A, B and Z above the amino or carbonyl (or acetalized formyl) groups $R^1$ and $R^2$ in compounds of formulae II and III which participate in the formation of the Schiff base type bond are connected to the residues A and/or B either via the bivalent organic group X and/or X' respectively or may be part of the residues A and B respectively, in which latter case X and/or X' in the resulting compound of formula I are/is absent.

It should be noted that at least one of the reacting carbonyl and amino groups is an aromatic group, viz. is directly connected to an aromatic group so that in a compound of formula I at least one aromatic group is directly adjacent to Z or that, alternatively, in case of an aliphatic carbonyl compound the amino compound is a hydrazide or hydroxylamino O-derivative.

Consequently, if in a compound A—X—$R^1$ (II) X has an aliphatic group adjacent to $R^1$, the reactive carbonyl or amino function $R^2$ in the compound of formula III must be an aromatic or araliphatic one, i.e. X' must have an aromatic group adjacent to $R^2$ or the amino function should be derived from hydrazine or hydroxylamine, while if X has an aromatic group adjacent to $R^1$ or the amino function is derived from hydrazine or hydroxylamine, the reactive carbonyl or amino function, $R^2$ in the compound of formula III may be adjacent either to an aromatic or aliphatic group, but aromatic is preferred.

The structure of the aliphatic or aromatic groups X' and/or X is not critical. The aromatic groups may be derived from a hydrocarbon or from a heterocycle; they are preferably derived from benzene, viz. either of them is or both are phenylene radicals which may be substituted. The only limitation with respect to the substituents of X' and/or X is that they should not interfere with the reaction of the amino or carbonyl group, i.e. should not react instead of the amino or carbonyl groups, should not be a sterical hindrance or should not deactivate the reactive groups.

Compounds of the following general formulae are examples of subgroups of compounds of the general formula I

| | |
|---|---|
| A—C(R)=N—X'—B | (I-E') |
| A—X—C(R)=N—B | (I-F') |
| A—C(R)=N—B | (I-G') |
| A—N=C(R)—X'—B | (I-E") |
| A—X—N=C(R)—B | (I-F") |
| A—N=C(R)—B | (I-G") |
| A—C(R)—NH—X'—B | (I-H') |
| A—X—C(R)—NH—B | (I-I') |
| A—C(R)—NH—B | (I-K') |
| A—NH—C(R)—X'—B | (I-H") |
| A—X—NH—CH(R)—B | (I-I") | and $$A-NH-CH(R)-B \tag{I-K"}$$

With R=hydrogen (i.e. with one of the reaction partners being an aldehyde or a protected aldehyde) compounds of the following subgroups of general formula I are obtained:

| | |
|---|---|
| A—CH=N—X'—B | (I-e') |
| A—X—CH=N—B | (I-f') |
| A—CH=N—B | (I-g') |

A—N=CH—X'—B (I-e")

A—X—N=CH—B (I-f")

A—N=CH—B (I-g")

A—CH$_2$—NH—X'—B (I-h')

A—X—CH—NH—B (I-i')

A—CH$_2$—NH—B (I-k')

A—NH—CH$_2$—X'—B (I-h")

A—X—NH—CH—B (I-i")

and

A—NH—CH$_2$—B (I-k").

The condensation between compounds II and III can be carried out in accordance with methods well-known in the art under mild conditions in dilute solutions. The reaction the most intensively studied was that of des-Ala$^{B30}$-insulin-B29-formylanilide with m-aminobenzoyl-ferrioxamine B. The most generally useful ranges of conditions are described immediately below. However, as will be seen from the appended Examples the reaction conditions are easily and successfully applicable to other reactants in spite of considerable differences in their nature.

The reaction can be carried out with good results at a pH range of 3.5–5.5. Any suitable aqueous buffer can be used. The buffer was normally aqueous acetic acid (1%, v/v) adjusted to the desired value with NaOH solution. Insulin derivatives are poorly soluble at the upper end of this pH range, but the addition of solid urea overcame this problem without any detectable effect on coupling efficiency. Dimethylformamide could also be used as a solubilizing agent, at the cost of some slowing down of the coupling. Similar problems with other protein derivatives may be overcome in a similar way.

The concentration of the insulin-aldehyde derivative was usually between 500 µM and 1 mM, that of the other reactant, m-aminobenzoyl ferrioxamine B, was usually between 500 µM and 2.5 mM. The reactants can be used in equimolar amounts or up to a multiple excess of one of the components.

Couplings can be carried out at ambient temperature. The half-time of these reactions, as judged by HPLC after quenching by dilution in acid, is of the order of one to two minutes. After 20–40 minutes yields are generally already at a maximum and the starting product is almost imperceptible.

The protein-carbonyl derivative can be used either as the free carbonyl compound or, especially in case of aromatic aldehyde, as an acetal, preferably as the methyl or ethyl acetal. The free compound still coupled efficiently after storage as a freeze-dried powder at room temperature for some months. In theory, the acetal-protected forms should have been deprotected before coupling, but it proved possible to take advantage of their lability to acid below pH 6 (which is far greater in case of aromatic acetals, than the lability of aliphatic acetals) and allow them to deprotect in the coupling mixture. If it turns out that at pH 5.5 no coupling occurs, the pH may be lowered. At pH 3.5 there will most probably be no difference in the reaction speed between the acetal protected form and the free aldehyde.

When of appropriate structure the compounds of the Schiff base-type obtained may be isolated and purified. It is well-known that Schiff bases are readily hydrolyzed and relatively unstable due to easy cleavage of the —CH=N-bond. However, in some cases such lability may be of advantage and, therefore, explicitly desired. Schiff base-type compounds obtained from two aromatic reactants (aromatic aldehyde group and aromatic amino group) are more stable than those obtained with one of the reactants being aliphatic. Oximes and hydrazones are more stable than simple Schiff bases.

Therefore, it is generally desirable to stabilize the Schiff base-type compounds. This is most conveniently done by reduction of the —CH=N-bond to a —CH$_2$—NH-bond and accomplished in a manner well-known in the art using complex metal hydrides, preferably sodium cyanoborohydride or pyridine borane. Only a small excess of cyanoborohydride is necessary and technical grade product can be used without disadvantage. Where a higher purity is desirable it can be purified by precipitation from acetonitrile by the method of Jentoft and Dearborn (J. Biol. Chem. 254, 4359–4365 [1979]). Otherwise, pyridine borane may be used (Wong et al., Anal. Biochem. 139, 58–67 [1984]).

The compounds of formula I (conjugates) obtained can easily be transformed into salts using methods well known in the art. In the case of conjugates wherein B is the residue of a chelating agent (chelon), metal salts, especially salts with radioactive metals are the desired end products useful as valuable tools in diagnosis and therapy. Every kind of radioactive salt can be obtained by simply mixing a protein-chelon conjugate with an appropriate solution of a radioactive metal and it is believed that the improved techniques for conjugation of proteins provided by the present invention will lead to improvements in radio-immunoassay technique, histo- and cytochemistry, and in vivo imaging. Once the protein-chelon conjugates have been prepared, they can be stored for long periods. It should subsequently be possible to label them whenever wished with alpha, beta, gamma, positron, and even neutron emitters under mild and strictly comparable conditions. The method will be equally applicable to NMR imaging with paramagnetic ions serving as contrast agents. If a gamma emitter is desired the protein may be labelled with $^{111}$In (specific activity >5000 Ci/mmol) while a suitable positron emitter is $^{68}$Ga (max. theoretical specific activity 2.7×10$^7$ Ci/mmol).

The protein or polypeptide derivatives of formula II which are used as starting materials in the coupling reaction of the present invention may be prepared by reacting a protein or polypeptide with a suitable bifunctional reagent using methods well known in the art. It is easily possible to, e.g. acylate side chain amino groups of proteins and polypeptides with bifunctional reagents. In that case when an aliphatic or aromatic compound of formula R$^3$—X—R$^1$ is used containing one function (R$^3$) capable of reacting with a reactive group of a protein side chain and a second reactive group R$^1$, wherein R$^1$ as well as X are as defined above, compounds of formula A—X—R$^1$ (II) are obtained wherein the protein or polypeptide residue is connected via a side chain. While in such a reaction, e.g., acylation will occur at several sites and a mixture of different compounds II will be obtained, it is preferable to use reaction conditions by which the point of attachment is limited to a single selected region of the protein or polypeptide. A preferred selected region in connection with the present invention is the carboxy terminus of the protein or polypeptide.

In recent years proteolytic enzymes have already been used in the synthesis of peptide bonds. This is possible because the enzyme catalyzed proteolysis is a reversible reaction. The method has been described by several authors (see e.g. Jakubke et al., Angew. Chemie, Int. Ed. Engl., 24, 85–93 [1985]) and has been used already successfully, e.g.

in the preparation of human insulin (see e.g. Rose et al., Biochem. J. 211, 671–676 [1983]; European published patent application No. 87 238). Especially suitable enzymes useful in such reverse proteolysis which can be used to prepare compounds which are the preferred coupling reagents in the process of the present invention are trypsin and carboxypeptidase Y. However, other enzymes can also be used, with the best reaction conditions being easily determined in some preliminary experiments.

The general reaction can be described by the following equation

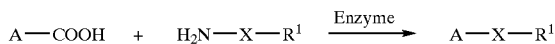

wherein A, X and $R^1$ are as defined above and the carboxyl group is the C-terminus of the molecule.

In specific examples the coupling of p-aminophenylalanine amide (with carboxypeptidase Y) and of m-amino-benzaldehyde methyl and ethyl acetal (with trypsin) to the C-terminal region of the B-chain of insulin is described below. These compounds are representations of bifunctional molecules of the general formula $R^3$—X—$R^1$ which are especially useful in connection with the present invention. In these and all following reactions no protection whatever was needed for the protein's functional groups. Under the semi-aqueous conditions that have been chosen for the trypsin-catalyzed reaction, synthesis is greatly favoured over hydrolysis. Only $Lys^{B29}$ is affected and the final product was des-$Ala^{B30}$-insulin-B29-m-formylanilide.

Normally, carboxypeptidase Y progressively attacks the C-terminus of proteins. Such a degradation can be carried out under conditions that favour synthesis at the same time as hydrolysis (Widmer et al. in Peptides 1980, 46–55 (editor K. Brunfeldt). Scriptor Kopenhagen [1981]; Widmer et al. in Peptides 1982, 375–379 (eds. Blaha and Malon), W. de Gruyter Berlin and New York [1983]). Under such circumstances, while a mixture is obtained, it is one in which useful products predominate. If large polypeptides and proteins are used the heterogeneity of the end product which may exist due to continuous degradation of the protein from the C-terminus or perhaps of the enzyme's inserting more than one molecule of compound $R^3$—X—$R^1$, is, however, of minor importance since it remains restricted to a small region, viz. the C-terminus, of the molecule and will generally not be crucial to its activity.

The above coupling principle which can be extended to all proteins of interest is of specific interest in view of its applicability to immunoglobulins, especially antibodies of the IgG type, and to fragments thereof, such as F(ab')$_2$ or Fab. Trypsin produces Fab-like fragments analogous to those made with papain, and the above equation applies to the fixation of a unique site for conjugation at the C-terminus thereof, a region known to be far from the antigen-binding site. It cannot be excluded that papain might also participate in such a coupling reaction and give directly the wanted derivatives of Fab fragments. Furthermore, carboxypeptidase Y will also introduce points of attachment (for the formation of Schiff base type, derivatives) at the C-termini of all the chains of IgG. F(ab')$_2$, and Fab molecules, once again far from the antigen combining sites.

The feasibility of the carboxypeptidase Y approach has been studied in extenso. The possible range of conditions in the coupling of p-amino-phenylalanine amide to insulin with carboxypeptidase Y was explored in the following manner:

An aqueous solution of p-amino-phenylalanine amide (10 mg/ml) was adjusted to the desired pH in the range 5.5 to 9.5 with either dilute NaOH or dilute HCl as necessary, and then freeze dried. This product could then be dissolved in water to produce a self-buffered solution at any desired concentration in the range from 0.1 M to saturation. For each set of conditions 4.5 μl of a solution of zinc-free insulin (20 mg/ml in 0.01 N HCl) was taken. 5.5 μl of buffer (0.1 M sodium phosphate) were added at the desired pH. The p-aminophenylalanine amide was then added in the form of 6.5 μl of self-buffered solution at the appropriate pH and the chosen concentration. Carboxypeptidase Y (1 μl of an aqueous solution of 2.14 mg protein/ml) was then added. If the solution was not clear (i.e. close to the isoelectric point of insulin), sufficient solid urea was added to clarify it. This system was used for the rapid exploration of a range of amide concentrations and reaction times. For each time point the degree of coupling and degradation was assessed in the first instance by quenching 2 μl of the reaction mixture in 100 μl of glacial acetic acid, diluting it to 1.7 ml in 0.01 N HCl, and applying 1 ml of the resulting solution for HPLC. Indications of success were confirmed by tests on the product isolated from larger scale digests after acid quenching by gel-filtration in 1% acetic acid. The reaction chosen was a Schiff base coupling with benzaldehyde and consecutive reduction with cyanoborohydride.

The best conditions found are: pH 8.5; a final concentration of p-amino-phenylalanine amide of 1.3 M; incubation from 7 to 22 hours at 20° C. Digestion at pH values higher than pH 8.5 led to much slower reaction, whilst digestion at pH values lower than pH 8.5 led progressively to more degradation and less useful synthesis. At pH 5.5, or at practically any pH in the absence of p-amino-phenylalanine amide, the concentration of carboxypeptidase Y used in the above tests led to rapid and extensive degradation.

Additional experiments indicated that contrary to what is advantageous when using trypsin as enzyme the addition of butane-1,4-diol up to 50% by volume gives little advantage in carboxypeptidase-mediated couplings with the alpha amino group of p-amino-phenylalanine amide, but increases the coupling yield when the attacking nucleophile is a benzylamine derivative.

The feasibility of the carboxypeptidase Y approach having been demonstrated with insulin, conditions will have to be optimized for each new protein. With relatively few trial experiments, it will prove possible to find conditions that give useful yields of derivatives capable of coupling.

Once made in bulk, the butane-1,4-diol solutions can be stored for very long periods. Aminobenzaldehydes being well known for the spontaneous polymerization between their amino and aldehyde groups, had to be protected at the aldehyde function until the amino function was protected by combination with the protein. The acetal protection was sufficiently stable to survive all the steps of the synthesis, but the resulting protein aldehyde acetals are so labile to acid that they can be deprotected under conditions mild enough to present no risk to the integrity of most proteins.

Another preferred selected region for the introduction of a complementary group (amino or carbonyl function) is the amino terminus of the protein or polypeptide.

Thus an N-terminal glycyl residue of a protein may be converted into an aldehyde function, by transamination, preferably by reaction with glyoxylate. This reaction proceeds under relatively mild conditions (see e.g. Dixon, H. B. F. and Fields, R., Methods in Enzymology, 25, 409–419 [1979]). The generality of this reaction may be extended by deliberately introducing Gly as N-terminal residue of proteins produced by recombinant DNA methods. In cases where Gly is not N-terminal, a useful keto group may nonetheless be formed by transmination of another N-terminal amino acid than glycine to yield the corresponding keto acid.

Furthermore, N-terminal Ser and Thr residues may be oxidized in an exceedingly mild reaction with periodate (e.g. 20° C. 26 μM protein, 1 mM imidazole buffer pH 6.95, 2-fold excess of periodate for 5 min). N-terminal Ser reacts about 1000 times as fast as other protein groups (Fields, R. and Dixon. H. B. F., Biochem. J. 108, 883 [1968]), so great specificity may be obtained. For greater generality, N-terminal Ser or Thr may be introduced by recombinant DNA techniques, or, in appropriate cases, by selecting a source of the protein of interest which has a natural Ser or Thr N-terminus.

The polypeptidyl N-terminal aliphatic aldehydes produced by these techniques may be reacted, preferably, with aromatic amines or with O-alkyl-hydroxylamines.

This invention also encompasses intermediate compounds of the formula A—X—R$^{1'}$ (II') and R$^{2'}$—X'—B' (III'), in which A, X and X' are as defined above, and R$^{1'}$ and R$^{2'}$ are defined as R$^1$ and R$^2$ are defined above, except that they may additionally be protected amino groups. B' in formula III' is a residue of DTPA, ferrioxamine B or desferrioxamine B, cuprioxamine B, polyglutamic acid and derivatives thereof or [N$^\epsilon$ (DTPA-alanyl)-Lys]$_n$, with n being an integer >1.

As discussed above (see page 10), preferred compounds of formula II are those wherein X is an aromatic or araliphatic radical or has O adjacent to the amino group where R$^1$ is amino or protected amino. Another preferred group of compounds of formula II are derivatives of immunoglobulins, i.e. those wherein A represents the residue of an immunoglobulin molecule, preferably of an IgG or antibody molecule, or of a fragment thereof such as an Fab or F(ab')$_2$ fragment. The preparation of the novel compounds can be effected according to methods well-known in the art, especially in the way described hereinbefore by reverse proteolysis.

The reaction partners of compounds II are compounds of formula R$^2$—X'—B (III) wherein R$^2$, X' and B are as defined above. If two proteins or a protein and a polypeptide are to be linked together (formation of homo- and hetero-dimers) B is the residue of a protein or a polypeptide. The proteins or polypeptides are coupled via an amino or carbonyl function already present in the molecule or which is introduced by methods know in the art. A formyl function may be present in protected form as an acetal, preferably in form of a methyl or ethyl acetal.

The keto, aldehyde or acetalized aldehyde function in compounds II und III may be introduced either directly using reactions well known in the art or indirectly in the form of a non-carbonyl precursor group which can be converted into a carbonyl function by known methods, such as the periodate oxidation of a diol residue (see Examples 7 and 17) or of a residue with vicinal hydroxy and amino groups.

Regarding the reaction partners of compounds II, i.e. the compounds of formula III as defined above, those compounds are of most importance in connection with the present invention wherein B is the residue of a chelating agent (chelon). Any compound which is capable of chelating metal ions can be used. If the chelating agent does already contain a group R$^2$, i.e. an amino or carbonyl function (in which case X' is absent), there is no need to introduce an additional functional group of that type and the chelon can be coupled directly to a compound of formula II above (unless it is wished to convert an aliphatic group R$^2$ to a preferred aromatic group R$^2$). 1-p-Aminophenylethylene-dinitrilo-tetraacetic acid (U.S. Pat. No. 3,994,966) is an example of such a compound which already contains an aromatic amino group. Other suitable chelating agents useful in the present invention and worth being mentioned are 1-amino-6,17-dihydroxy-7,10,18,21-tetraoxo-27-(N-acetylhydroxylamino)-6,11,17,22-tetraazaheptaeicosane, otherwise known as desferrioxamine or deferoxamine (in its iron-bound form known as ferrioxamine B) and diethylen-etriaminepentaacetic acid (DTPA; Krejcarek et al., Biochem. Biophys. Res. Commun. 77, 581–585 (1977)). These latter two chelating agents may be converted into preferred derivatives R$^2$—B by methods well known in the art.

Hitherto, desferrioxamine has been attached to proteins by means of random coupling to side-chain amino groups, brought about either by glutaraldehyde (Janoki et al., Int. J. Appl. Radiat. Isot. 34, 871–877 [1983]) or by water-soluble carbodiimide (Janoki et al., J. Nucl. Med. 24, 909 [1982]). These papers, while fully demonstrating the excellence of the choice of that chelon, also indicated the need to look for milder, more specific methods of coupling.

Ferrioxamine B is much more soluble than its iron-free form, desferrioxamine. Because it is more difficult to follow the syntheses with the iron-free compounds, since chromatography tends to be difficult, and there is also the danger that the hydroxylamino groups, if not protected by chelation, might participate in side reactions, ferrioxamine B instead of the iron-free compound was used to produce protein conjugates. Then the iron was removed with acid/EDTA and the metal-free form of the conjugate was stored until needed. This approach proved satifactory, as judged by the fact that the protein conjugate treated in this way could be loaded with $^{111}$In and $^{68}$Ga, whilst a protein conjugate that still had its iron could not be loaded. Therefore, ferrioxamine B by use of the following reaction sequence (Scheme 1) was transformed to m-aminobenzoyl-ferrioxamine B which is an example of a compound of general formula III and very useful as coupling partner in the process of preparing protein or polypeptide derivatives in accordance with the present invention.

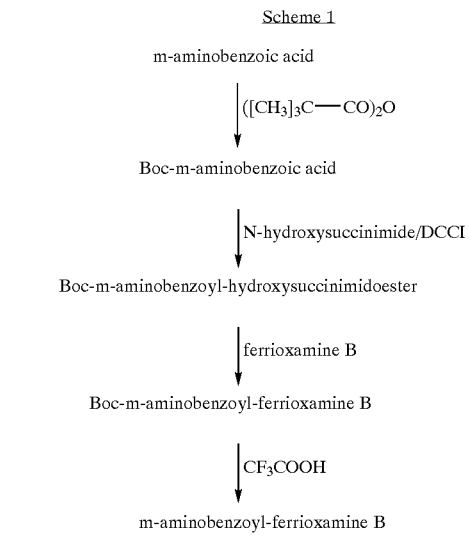

Scheme 1

Instead of m-aminobenzoyl-ferrioxamine B there can also be used the analogous compound wherein the iron ion is replaced by Cu$^{2+}$. This latter ion is sufficiently weakly bound to be replaced by other metals such as Fe$^{3+}$ but otherwise strongly enough to remain in the complex during all the other operations described above.

The preparation of m-aminobenzoyl-ferrioxamine B and its coupling to an insulin derivate are described in detail in Examples 1(b) and (c) respectively (below). The copper analogues of these compounds can be made in an analogous manner to that described therein.

Cuprioxamine B is made precisely analogously to the published method for the iron complex (Prelog, V. and Walser, A., Helv. Chim. Acta 45, 631–637 [1962]) with an equivalent quantity of cupric chloride instead of ferric chloride used in that publication. The intermediate products, as well as the final m-aminobenzoyl-cuprioxamine B are all light green in colour. Their $R_f$ values on thin-layer chromatography (t.l.c.) are all identical to those of the iron compounds.

Unlike in case of m-aminobenzoyl-ferrioxamine B, removal of the metal is not necessary before loading with another metal in the case of m-aminobenzoyl-cuprioxamine B. The binding constant of copper in the complex is many orders of magnitude lower than that for metals such as iron and gallium, which displace the copper almost instantly in dilute, neutral or mildly acid solution.

DTPA has usually been attached to proteins either by means of its bis-anhydride (e.g. Layne et al., J. Nucl. Med. 23, 627 [1982]), or by a mixed-anhydride method (Krejcarek and Tucker, Biochem. Biophys. Res. Comm. 77, 581 [1977]). In both cases, the coupling to the side chains of the target protein is random. In addition the bis-anhydride is capable of reacting with more than one amino group at a time, and does so to a considerable extent. This reagent is also very rapidly hydrolysed in aqueous media, and although this has not greatly hindered its exploitation so far, it could nonetheless be a complicating factor under some circumstances. Paik et al., J. Nucl. Med. 24, 932 (1983) formed a mixed anhydride between carefully controlled quantities of DTPA and isobutylchloroformate. However, as with the original work of Krejcarek and Tucker (supra) they were unable to avoid the formation of statistical mixtures of products, no matter what ratio of reactants was chosen. The mixed anhydride, too, was labile to water.

Therefore, in accordance with the present invention an activated derivative of DTPA was chosen that, because of its stability, could be purified from its bi-reactive form. This derivative is DTPA-mono-(m-formylanilide) (or its dimethyl or diethylacetal) the preparation of which is shown in the following scheme.

Scheme 2 m-aminobenzaldehyde diethylacetal

↓ DTPA-bis-anhydride

-continued

DTPA-mono-(m-formylanilide) diethylacetal

+

DTPA-bis-(m-formylanilide) bis-diethylacetyl

↓ (i) acid treatment
(ii) separation by HPLC

DTPA-mono-(m-formylanilide)

While mention was made above of the desirability of keeping ferrioxamine B in its metal-bound form until the end of the synthesis of the protein-chelon conjugate, no such difficulty presents itself with the DTPA derivative. The synthesis can be carried out with metal-free compounds, and the final protein conjugate could be loaded with the desired ion without difficulty.

An example of very powerful compounds of formula III in terms of chelating activity, containing a polymeric chelon, ready to couple by the Schiff base method of the present invention are compounds of the formula m-$NH_2$—$C_6H_4$—CO—[$N^\epsilon$-(DTPA-alanyl)-Lys]$_n$, wherein n is are integer >1. The preparation of such a compound with n=5 and its coupling is described in detail in Example 6 below. Another compound of that type is, e.g., polyglutamic acid to which ferrioxamine B is coupled up to one ferrioxamine B per side chain carboxy group (see Example 15 below). However, in analogy to polyglutamic acid and derivatives thereof other polymeric compounds, especially polypeptides, may be used to form compounds of formula III of the present invention.

Finally, another monovalent derivative of the chelating group DTPA which can be used for labelling of polypeptides and proteins is DTPA-alanine-p-nitrophenylester, i.e. a compound of the following formula

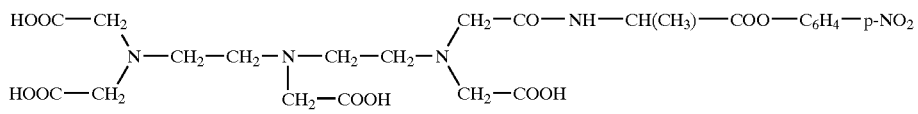

This compound can be prepared in the following manner:
To 2 ml of aqueous 1 M sodium acetate buffer, pH 5.5, were added 50 mg of Ala-p-nitrophenylester.HCl under vigorous vortex mixing at room temperature. As soon as the material had dissolved, 84 mg of DTPA-bisanhydride were added under further vigorous vortex mixing. The anhydride dissolved over a period of about two minutes. At this point the reaction mixture was injected onto a preparative HPLC column (250×16 mm, packed with 7 μm LICHROSORB RP-8 particles) previously equilibrated with 0.1% (w/v) trifluoroacetic acid in water. The column was eluted at 2 ml/min with the same solvent for 5 min, whereupon a biphasic linear gradient of pure acetonitrile was applied, the first phase reaching 35% acetonitrile after 35 minutes and the second reaching 55% acetonitrile after 85 minutes total time. The eluent was held at 55% acetonitrile for 5 minutes before being programmed down linearly to 0% over 10 min. The effluent was monitored at 214 nm. The desired product was collected at retention time 57–62 min and the dimeric product, due to the acylation of two molecules of Ala-p-nitrophenyl ester by the bis-anhydride, eluted at retention time 74–95 min. After removal of acetonitrile at room temperature on a rotary evaporator, the product was recovered by lyophilisation (yield ca. 40 mg). The product was examined by FAB-MS and by analytical HPLC on a RADI- ALPAK μBONDAPAK C-18 cartridge with a linear gradient of pure acetonitrile (0–60%, v/v, 2% per min.) after 5 minutes in 0.1% (v/v) aqueous $CF_3COOH$. The desired product eluted at retention time 25 min under these conditions. Some batches which contained a contaminant, identified by FAB-MS as possessing an extra alanyl residue but only one nitrophenylester group and eluting from the analytical column at retention time 26 min were repurified on the preparative column (see Example 1(c)). Yield from 50 mg Ala-p-nitrophenylester.HCl: ca. 24 mg. The final product was pure by analytical HPLC and gave the expected FAB-MS spectrum (protonated molecular ion at m/z 586, sodium-cationised ion at m/z 608 and potassium-cationised ion at m/z 624).

The above mentioned compounds, wherein a chelating agent has been modified in order to make it suitable for a condensation reaction yielding Schiff bases, are still novel and, therefore, are also part of the present invention.

EXAMPLES

The following examples illustrate but in no way limit the present invention.

Example 1

(a) Preparation of des-Ala$^{B30}$-insulin-B29-m-formylanilide

Tris-HCl (16 mg) was crushed in 3 ml butane-1,4-diol contained in a centrifuge tube. The suspension was thoroughly mixed and the crystals that had not dissolved were centrifuged to the bottom of the tube. To 1.162 ml of the supernatant was added 260 mg of m-aminobenzaldehyde dimethyl acetal, and the mixture was agitated on a Vortex mixer. (In a second experiment the corresponding diethyl acetal was used.) After addition of 30 μl of N-ethylmorpholine (redist.) and further agitation, the pH of the solution was measured with a glass electrode and adjusted to 6.2 by successive additions of 10% (v/v) acetic acid in butane-1,4-diol. Because of the acid-lability of the acetal, the acid was added very cautiously, with vigorous mixing. Particular care was needed once the pH had fallen below 6.5. The resulting solution could be stored frozen, at −20° C., for many months.

The buffered acetal solution (300 μl) was added to 20 mg of Zn-free insulin (Rose et al., Biochem. J. 211, 671 [1983]), followed by 10 μl of water. The insulin normally went into solution during a 1 h incubation at 38° C., with only occasional, mild agitation. Once the insulin was in solution, 10 μl of a freshly made solution of TPCK-treated trypsin (5 mg in 40 μl) was added, and incubation was continued at 37° C. The progress of the coupling was followed by cellulose-acetate electrophoresis (pH 8) as described by Rose et al., Biochem. J. 195, 765 [1981] or by HPLC (250×4.6 mm RP-18 SPHERI 5 column with a linear gradient of 3.5 to 35% (v/v) acetonitrile in 0.3 M ammonium sulfate in 7 minutes). The reaction product migrated more slowly than insulin on electrophoresis, and emerged two minutes after insulin on HPLC. As judged by either criterion, the ratio of insulin to product was about 1:2.5 in favour of the latter after, typically, 3 h of incubation. As seen by HPLC some other protein peaks appeared progressively during the incubation, but the largest of them only represented 14% of the total protein by the end.

The reaction mixture was cooled and 3.1 ml of glacial acetic acid were added to stop the enzymic reaction. The resulting mixture was then diluted with an equal volume of 10% (v/v) acetic acid and subjected to gel filtration on a 90×2.6 cm column of SEPHADEX G-50 (fine), elution with 1% acetic acid.

The fractions containing the insulin derivative were pooled and lyophilized. The product was further purified by ion-exchange chromatography (column 2×20 cm A-25, Pharmacia) equilibrated with 7M urea-100 mM tris, adjusted to pH 8.4 (glass electrode, urea already present) with 12M HCl. Elution was carried out by means of a linear gradient (1 liter total) between this starting buffer and one identical except for the presence of NaCl (200 mM). The fractions is of the first peak to emerge were pooled and dialysed against 1% (v/v) acetic acid.

If it was wished to preserve the acetal (normally only in the case of the slightly more stable methyl form), then the trypsin was stopped by diluting the incubation mixture into 5 ml of the A-25 column starting buffer and applying the solution directly to the A-25 column. In this case most conditions were as given above except that the gradient was from 0 to 155 mM NaCl. The trypsin passed through the column at once, together with the m-aminobenzaldehyde dimethylacetal and its side products. The wanted product emerged early in the gradient, about 4 column volumes after the initial breakthrough. Assay showed that the desired product was nonetheless uncontaminated by any trypsin activity. With the exception of unchanged insulin, which emerged much later in the gradient, the wanted product was the only significant protein peak. The pooled product fractions were dialysed against 0.5% (w/v) aqueous $NH_4HCO_3$ and freeze-dried.

The products could be further purified (from rather minor contaminants) by HPLC (250×4.6 mm RP-18 Spheri 5 column with a linear gradient of 3.5 to 35% (v/v) acetonitrile in 0.3 M ammonium sulfate in 7 minutes), loading of up to 5 mg at a time. The eluant was sufficiently acidic to deprotect any acetalized protein during the separation. The chromatographic behavior of acetalized and non-acetalized insulin derivatives was identical.

Characterization of the product:

The compound obtained (after acid-treatment to remove putative acetal protection) was coupled to m-aminobenzoic acid to yield a Schiff base in the usual way (see Example 1(c)). If tritiated borohydride was used to reduce the Schiff base, tritium was incorporated into the protein fraction. The reduced product migrated on cellulose-acetate (pH 8) as though it had regained the —COOH group lost by replacement of the C-terminal alanine by the m-formyl-benzaldehyde, and the band of reduced product showed the characteristic blue fluorescence of m-aminobenzoates. Digestion with Armillaria protease gave a product with the expected paper-electrophoretic properties.

(b) Preparation of m-aminobenzoyl-ferrioxamine B

Ethyl acetate (10 ml) was added to 125 mg of m-aminobenzoic acid (purum). N-Ethyl morpholine (redist., 200 μl) was added to the mixture, followed by 1 ml of di-tert.-butyl dicarbonate (purum). The faintly cloudy solution clarified on stirring overnight at 20° C. The mixture was then extracted three times with 10 ml of 0.3 M $NaHCO_3$ and the pooled aqueous layers were cooled and acidified by addition of an equal volume of cooled 0.6 M citric acid. A precipitate formed at this point, which disappeared when the suspension was extracted with 15 ml of ethyl acetate. After separation of the phases, the aqueous layer was re-extracted with 5 ml of ethyl acetate and the two organic layers combined. The pooled organic fraction was allowed to stand overnight over $MgSO_4$. The solution was then dried, first by rotary evaporation, then in a desiccator (NaOH pellets) under an oil-pump vacuum. Some 80 mg of this product were dissolved in 252 82 l of dimethylformamide, together with 42.6 mg of N-hydroxysuccinimide. To this solution were added 76.4 mg of dicyclohexylcarbodiimide in 63 µl of dimethylformamide, and the mixture was allowed to stand overnight under agitation. A precipitate began to form at once, and by the following morning was extremely dense. TLC of the supernatant showed virtually complete conversion to a product having the expected migration of a Boc-m-aminobenzoic acid hydroxysuccinimido ester. The precipitate was removed by centrifugation and the supernatant dried in a vacuum desiccator over NaOH pellets under an oil-pump vacuum. The slightly waxy solid thus obtained was used in the following reaction without further purification.

To 4 ml of a 0.4 M aqueous solution of ferrioxamine (343.8 mg) was added an equal volume of dimethylformamide. N-Ethylmorpholine was then added until the pH (estimated externally on moist pH paper) rose above 8. About 300 µl of the base were required. To this mixture was then added 196 mg Boc-m-aminobenzoic acid hydroxysuccinimido ester dissolved in 4 ml of dimethylformamide. After ascertaining that the pH had not changed noticeably, the mixture was left overnight at 20° C. The following morning 12 ml of distilled water were added to the reaction mixture, and the solution was extracted three times with 24 ml (each time) of chloroform. The pooled organic layers were extracted twice with 3.2 ml (each time) of water. The organic phase was dried on a rotary evaporator. The product was characterized by FAB-MS. The Boc-group was removed by dissolving the residue in 7 ml of 98–100% formic acid. After 30 min. the deprotected product was isolated by HPLC (250×16 mm columnm filled with 7µ LICHROSORB RP-8, linear gradient between 15% and 45% acetonitrile over 30 min. in 0.1% (v/v) aqueous $CF_3COOH$, at a flow rate of 2 ml/min). The desired product (222 mg, 54% yield) was in the first major peak (retention time 35.5 minutes) to emerge after the injection transient and was characterized by FAB-MS. A second peak emerged after 42.5 minutes, and was found by mass spectrometry to be the N-formyl derivative of the desired product. A third peak (retention time 56.5 min) contained non-deprotected starting product.

The degree of N-formylation can be considerably reduced by working at a lower concentration of the Boc-derivative (12 mg/ml). It is also possible to remove the formyl group by treatment with 0.1 M HCl at room temperature, monitoring the progress of the removal by HPLC.

The above preparation can be followed by TLC. In n-butanol/acetic acid/pyridine/water (15:3:12:20, v/v) on KIESELGEL 60 (Merck) the respective $R_f$-values are:

| | |
|---|---|
| ferrioxamine | 0.27 |
| m-aminobenzoyl-ferrioxamine B | 0.44 |
| N-formyl-m-aminobenzoyl-ferrioxamine | 0.48 |
| Boc-m-aminobenzoyl-ferrioxamine | 0.56 |

(c) Preparation of des-Ala$^{B30}$-insulin/ferrioxamine B Conjugate 1 mg of des-Ala$^{B30}$-insulin-B29-m-formylanilide was dissolved in 45 µl of a 5.5 mM solution of m-aminobenzoyl-ferrioxamine B in a 1% (v/v) aqueous acetic acid buffer brought to pH 3.5 with strong NaOH solution. To this solution was added 20 µl of aqueous 2.4 mM sodium cyanoborohydride and 50 µl of water.

After 20 min. it was checked by HPLC that the reaction was terminated and the reaction product, des-Ala$^{B30}$-insulin-B29-NH—$C_6H_4$-m-$CH_2$—NH-m-$C_6H_4$—CO-ferrioxamine B, was isolated by HPLC using a 250×4.6 mm RP-18 SPHERI 5 column (Brownlee Laboratories, 2045 Martin Ave., Santa Clara, Calif. 95050, USA) and a linear acetonitrile gradient in 0.3 M aqueous ammonium sulfate over 30 min. The gradient was made by a two pump system with 0.3 M ammonium sulfate as solvent A (equilibration) and 0.3 M ammonium sulfate/35% (w/v) aqueous acetonitrile. The two solvents were made up using stock solutions of 3 M ammonium sulfate which had been adjusted to an indicated pH of 2.7 (glass electrode) by careful addition of conc. $H_2SO_4$. Elution was at 1 ml/min.

After removal of acetonitrile in a current of air, the is pooled fractions containing the insulin conjugate (a pale red solution) were worked up on a SEP PAK cartridge (Waters Associates, Milford, Mass. 01757, USA) according to the manufacturer's instructions. After a first wash with 10% (v/v) aqueous acetonitrile elution was effected with 40% (v/v) aqueous acetonitrile. The concentrated product was lyophilized after blowing off the acetonitrile. The peach-coloured solid was found to be homogeneous on cellulose acetate (pH 8) and HPLC RADIALPAK µ BONDAPAK C-18 cartridge in a Z-module, linear gradient of pure acetonitrile (0–60%) in 0.1% (v/v) aqueous $CF_3COOH$). The product was further characterized by FAB-MS of Armillaria protease digest. Digestion was carried out at pH 7.8 in 1% (w/v) ammonium hydrogen carbonate. This protease is known to cleave specifically on the amino-terminal side of Lys$^{B29}$ of insulin.

Example 2

Removal of Iron from the des-Ala$^{B30}$-insulin/ferrioxamine B Conjuate

To 225 µl of a 138 µM solution in water of the des-Ala$^{B30}$-insulin/ferrioxamine B conjugate obtained according to Example 1 were added 25 µl of 1 M propionic acid and 2 µl of 0.01 M EDTA and the mixture was adjusted to pH 3 with diluted HCl. The pink colour of the solution was rapidly lost. If desired the reaction can be followed spectroscopically, since after removal of iron the peak between 400 nm and 450 nm, characteristic of the ferrioxamine B conjugate will disappear completely. Such spectroscopy with a test solution of 1 mM ferrioxamine B showed that the half-time for the removal of iron at pH 3 was approximately 90 seconds, whilst that at pH 3.5 was approximately 340 sec. The reaction at pH 2.5 was too rapid to follow.

Once the iron had been removed, the solution was adjusted to pH 5.5 with 1.7 M sodium acetate buffer. The resulting precipitate was carefully washed by centrifugation in 0.7 M sodium acetate buffer, until the residual EDTA concentration could be expected to be negligible compared to that of the conjugate. It was found that such traces as persisted could not compete significantly for $^{68}$Ga and $^{111}$In under the labelling conditions described below. The iron-free protein derivative was stored as a frozen pellet for months without apparent impairment of its capacity to be labelled.

Example 3

Labelling of the des-Ala$^{B30}$-insulin/desferrioxamine B Conjugate with Radioactive Metals The des-Ala$^{B30}$-insulin/desferrioxamine B conjugate obtained according to Example 2 was dissolved or suspended at a concentration of 7 μg/μl in a buffer made by mixing equal volumes of 0.1 M ammonium acetate and 0.1 M sodium citrate and adjusting the resulting solution to pH 8.5–9 with 33% (w/v) aqueous ammonia. The radioactive metal solution ($^{111}$In Cl$_3$ or $^{68}$GaCl$_3$) was added to the buffer solution at a concentration of between 1 μCi and 1 mCi/μl just before the protein. The reaction mixture can be used directly in all further tests.

The degree of labelling can be determined immediately using radioactive techniques such as scintillation radioactive counting, radioactivity scanning, and radioautography on standard X-ray film after HPLC or cellulose acetate electrophoresis (pH 8).

Example 4

(a) Preparation of des-Ala$^{B30}$-insulin-B29-p-aminophenylalanine-methylester p-Amino-L-phenylalanine-hydrochloride.1/2 H$_2$O (Bachem, Bubendorf, Switzerland) was dissolved with agitation in 8.5 M HCl/MeOH at about 140 mg/ml and incubated overnight at room temperature. The reagents were removed under a stream of nitrogen and finally under high vacuum to yield as a crisp white powder p-amino-L-phenylalanine-methylester-hydrochloride. The reaction was quantitative as determined by TLC (butanol/acetone/acetic acid/water, 7:2:7:4, v/v) and cadmium-ninhydrin as the stain.

The $R_f$ of the starting material was 0.28; that of the product was 0.52.

208 mg of p-amino-L-phenylalanine-methylester.HCl were dissolved in 2 ml of butane-1,4-diol. To this solution were added approximately 2 ml of 0.5 M tris-base in butane-1,4-diol/H$_2$O (4:1, v/v), until the pH (glass electrode) was 6.5. 100 mg of solid Zn-free insulin were added to 3.1 ml of the buffered methyl ester solution. Most of the insulin went into solution after incubation at 37° C. for 30 minutes. Trypsin (12 mg, Worthington TPCK grade) was dissolved in 120 μl of water and 100 μl of the solution were added. After 90 minutes at 37° C., during which time the insulin dissolved completely, cellulose-acetate electrophoresis at pH 8 revealed that more than half of the insulin had been converted to a product that migrated more slowly than insulin. Since the pK of an aromatic amino group is well below 8, this is the expected behaviour of the desired product. The reaction mixture was cooled and 3.1 ml of glacial acetic acid were added to stop the enzymic reaction. The resulting mixture was then diluted with an equal volume of 10% (v/v) acetic acid and subjected to gel filtration on a 90×2.6 cm column of Sephadex G-50 (fine), elution with 1% (v/v) acetic acid.

The fractions belonging to the peak of the derivative were pooled and lyophilized. The product was further purified by ion-exchange chromatography (column 2×20 cm A-25, Pharmacia) equilibrated with 7 M urea-100 mM tris, adjusted to pH 8.4 (glass electrode, urea already present) with 12 M HCl. Elution was carried out by means of a linear gradient (1 liter total) between this starting buffer and one identical except for the presence of NaCl (200 mM). The first peak to emerge was pooled and dialysed against 1% (v/v) acetic acid. After lyophilization, 54.5 mg of des-Ala$^{B30}$-insulin-B29-p-aminophenylalanine-methylester were obtained.

The product gave a single peak on HPLC RADIAPAK μ BONDAPAK C-18 cartridge in a Z-module, linear gradient of 25–45% (v/v) acetonitrile in 0.1% (v/v) aqueous CF$_3$COOH over 20 minutes). The product migrated on cellulose-acetate electrophoresis at pH 8 as a single spot, in the expected position, i.e. migrated more slowly than insulin. On electrophoresis at pH 1.9, well below the pK of an aromatic amino group, the product migrated faster than unmodified insulin, consistent with its possessing an extra positive charge at this pH. Digestion of the product with trypsin released des-octapeptide-(B23–B30)-insulin (which was identified by HPLC and by electrophoresis on cellulose-acetate at pH 8), the heptapeptide comprising residues B23–B29 (which was identified by HPLC, by paper electrophoresis at pH 6.5, and by FAB-MS) and free m-aminophenylalanine-methyl-ester (which was identified by HPLC and by paper electrophoresis at pH 6.5).

(b) Preparation of DTPA-mono-(m-formylanilide)

Both Dowex-50 (WX-4, H-form) and pumice boiling stones were washed by filtration in 20 volumes of ethanol. Both were then boiled in 5 volumes of ethanol for 3 min., filtered, and dried in a vacuum desiccator. To 1 g of dried DOWEX-50 was added 13.5 g m-nitrobenzaldehyde (purum) and a copious quantity of boiling stones. Methanol (125 g) was added and the mixture was refluxed for 60 min. The mixture was then cooled and filtered. Approximately 70 ml of 0.2 M sodium carbonate-bicarbonate buffer, pH 9.5, were added. The aqueous phase of the resulting emulsion was extracted with 40 ml and 35 ml of ethyl acetate. The organic layer was dried for some hours over freshly baked K$_2$CO$_3$, filtered and evaporated to a syrup. TLC on KIE-SELGEL 60 (Merck) with CHCl$_3$/MeOH (9:1, v/v) showed a change in $R_f$ consistent with complete conversion to the dimethyl acetal ($R_f$=0.68 before, 0.73 after).

In an analogous way by refluxing 13.5 g of m-nitrobenzaldehyde with 125 g of ethanol for 30 min. the corresponding diethyl acetal was prepared which was easier to isolate. Since ethanol forms azeotropic mixtures with water, 60 ml could be removed by distillation while the DOWEX catalyst was still present (there was no need to add alkali). The residue, after filtration, was taken down to a syrup on a rotary evaporator.

The reduction of the nitro to the amino compound followed the method proposed by Howarth and Lapworth, J. Chem. Soc. 121, 76–85 (1922), for the diethyl acetal.

50 g of Na$_2$S (puriss.) were dissolved in 50 ml of water and 25 g of 12 M HCl were added slowly, with stirring. The resulting solution was added, with stirring, to a solution of 15 g of the dimethyl acetal in 90 ml of methanol (ethanol for the diethylacetal). Reaction was completed by refluxing for 6 h, after which the alcohol was distilled off from the deep red solution. The aqueous residue was cooled and extracted twice with 30 ml of diethylether. The ether layer was dried over MgSO$_4$, filtered and dried by rotary evaporation. The dimethyl and diethyl acetals could be stored, over periods of several months, without visible decomposition or polymerization, at room temperature in the dark.

To 20 mg of m-aminobenzaldehyde diethyl acetal was added 1 ml of pyridine followed by 1 ml of water. The resulting solution was slowly added to 200 mg of diethylene-triamine pentaacetic acid (DTPA) dianhydride (Calbiochem, La Jolla, USA) whilst Vortex mixing continuously to dissolve the anhydride.

After standing 15 min. at room temperature, the solution was cooled externally with ice whilst 2 ml of acetic acid were added. After 1 h at room temperature the sample was applied (two separate runs) to an HPLC system which has already been described by Rose et al., Biochem. J. 220, 189

(1984). A RADIALPAK μBONDAPAK C-18 cartridge was used, equilibrated with 0.1% (v/v) aqueous trifluoroacetic acid. The flow rate was 2 ml/min. Once the pyridine acetate had eluted (monitoring absorbance at 214 nm) after 30 min., a linear gradient of pure acetonitrile (increase 2% per min. up to 60%, v/v) was applied to elute the two major fractions. Together these fractions account for more than 90% of the absorbance at 214 nm appearing after the reagent front, and they are the only ones to give a precipitate with 2,4-dinitrophenyl hydrazine. Rotary evaporation of the acetonitrile followed by lyophilisation yielded 9 mg of first fraction and 8.5 mg of second fraction. Analytical high voltage paper electrophoresis was performed at pH 6.5. The spots, ninhydrin negative, were revealed by spraying with a saturated solution of 2,4-dinitrophenylhydrazine in 2 M HCl.

Paper electrophoresis at pH 6.5 showed the first HPLC fraction to have a relative mobility (m) of −0.72 (m of aspartic acid=−1.0), and the second fraction had an m-value of −0.34. The first HPLC fraction was considered to be the result of acylation of one molecule of m-aminobenzaldehyde followed by hydrolysis of the second anhydride moiety, and the second HPLC fraction was considered to be the result of acylation of two molecules of m-aminobenzaldehyde by the DTPA-dianhydride. This interpretation was confirmed by the FAB-MS spectra of the two fractions, which contained signals due to protonated molecular ions at m/z 497 and 600, respectively, and showed that, as expected, the acetal protection had been removed by the acidic conditions of the work-up.

(c) Coupling Between des-Ala$^{B30}$-insulin-B29-p-aminophenylalanine-methylester and DTPA-mono-(m-formylanilide)

The DTPA-m-aminobenzaldehyde was dissolved in the pH 3.5 buffer of Example 1(c) at a concentration of 5 mM (2.64 mg/ml). 10 mg of des-Ala$^{B30}$]insulin-B29-p-aminophenylalanine-methylester were dissolved in 450 μl of this solution and 500 μl of 10 mM NaBH$_3$CN were added. A precipitate (later identified as the desired product) began to form at once. After 15 minutes the precipitate was brought back into solution by cautious addition of glacial acetic acid, and diluted to approximately 1.5 ml with 0.1% (v/v) aqueous CF$_3$COOH. The mixture was subjected to HPLC RADIAL-PAK μBONDAPAK C-18 cartridge in Z-module, isocratic 5 min., then linear gradient of 25–45%, v/v, acetonitrile in 0.1%, w/v, aqueous CF$_3$COOH over 20 min.). The desired product emerged after about 17 minutes, and was the first peak after the injection transient. The acetonitrile was evaporated in a stream of nitrogen and, after lyophilisation, 9 mg of product were obtained. The product was homogeneous on HPLC and also on cellulose-acetate electrophoresis at pH 8. It gave a spot in the latter system which migrated faster than insulin towards the anode. After labelling with excess non radioactive In$^{III}$ and work-up on a SEP PAK, the product was characterized by digestion with trypsin followed by HPLC.

Example 5

Labelling of the des-Ala$^{B30}$-insulin-B29-p-aminophenylalanine-methylester/DTPA-mono-(m-formylanilide) Conjugate with Radioactive Metals The des-Ala$^{B30}$-insulin-B29-p-aminophenylalanine-methylester/DTPA-mono-(m-formylanilide) conjugate obtained according to Example 4 was labelled with $^{111}$In and $^{68}$Ga in the same manner as described in Example 3 for the des-Ala$^{B30}$-insulin/deferoxamine conjugate.

Example 6

(a) Preparation of m-aminobenzoyl penta-[(N$^\epsilon$-DTPA-alanyl)-lysine]

N$^\alpha$-Carbobenzoxy-penta-[(N$^\epsilon$-Boc)-lysine] (Bachem, Switzerland) was dissolved in anhydrous trifluoroacetic acid at a concentration of 25 mg in 750 μl. After 30 min. at room temperature, the trifluoroacetic acid was removed by evaporation. Further traces of acid were removed by redissolving the solid in anhydrous methanol (10 μl of MeOH for every mg of starting product). The product now gave a ninhydrin-positive spot on paper electrophoresis, having the expected mobilities at pH 1.9 and 6.5. A quantity of the dried acid-treated material equivalent to 8.5 mg of starting product was dissolved in DMSO (21 μl), 34 mg of DTPA-alanine-p-nitrophenyl ester were added, followed by 42 μl of DMSO. The apparent pH was then adjusted to 8 (moist pH paper) with N-ethyl morpholine (approx. 35 μl).

The reaction was followed by paper electrophoresis at pH 6.5 and was judged complete after 25 h (progressive replacement of the starting product with ever more acidic spots with ever fainter ninhydrin colour, finally virtual disappearance of all ninhydrin colour). The reaction mixture was lyophilized and re-dissolved in conc. aqueous HBr (45 μl for each mg of the protected penta-lysine starting material). After 30 min. at 20° C., the sample was dried down. It was then re-dissolved in 1% acetic acid (at a concentration of 10 mg/ml) and passed down a column of SEPHADEX G-25 (8 mm internal diameter, 60 cm long). The wanted product, penta-[(N$^\epsilon$-DTPA-alanyl)-lysine], emerges in the breakthrough volume. It had the expected mobility on paper electrophoresis at pH 6.5. The SEPHADEX pool was lyophilised A quantity of this product, equivalent to 10 mg of protected penta-lysine, was taken up in 166 μl DMSO and 26 mg of Boc-m-aminobenzoyl-hydroxysuccinimido-ester added, followed by 4 μl N-ethyl-morpholine. After 15 h at 20° C., the original ninhydrin colour on electrophoresis disappeared. After treatment of the dried reaction mixture with 750 μl trifluoroacetic acid and subsequent drying, the ninhydrin colour returned at approximately the same electrophoretic position (as expected) but as a much fainter, but much more rapidly developing, yellow colour (characteristic of an aromatic as opposed to an aliphatic amino group).

(b) Preparation of Conjugate between m-aminobenzoyl penta-[(N$^\epsilon$-DTPA-alanyl)-lysine] and des-Ala$^{B30}$-insulin The crude product obtained under (a) was used directly as a 7 mM solution for coupling to the product of Example 1(a) in exact analogy to the method of Example 1(c) to yield the desired conjugate. The new protein derivative has the expected intense blue fluorescence, and a mobility on cellulose-acetate electrophoresis at pH 8.3 of approximately 1.5 times that of the starting insulin derivative. The product was labelled with $^{111}$In according to the method of Example 3. Titration of the product with $^{111}$In of low specific activity using cellulose acetate electrophoresis to distinguish between protein-bound and protein-free indium suggested that nearly all of the DTPA groups are labelled when the appropriate quantity of $^{111}$In is presented to the protein at a concentration of approximately 10 pM.

Example 7

(a) Preparation of S-(2,3-dihydroxypropyl)-cysteamine

Cysteamine hydrochloride (1.08 g) and dithiothreitol (1.46 g) were dissolved in 100 ml of ammonium bicarbonate (2%, w/v) and allowed to stand at room temperature for 15 minutes. 3.1 g of 3-bromo-1,2-dihydroxy-propane were added. The alkylation of the thiol group was followed by paper electrophoresis at pH 1.9 (methods described by Gonzales and Offord, Biochem. J. 125, 309–317 (1971)). After 29 hours at room temperature, the cysteamine spot (staining yellow with ninhydrin) had been converted almost exclusively into a spot (staining grey with ninhydrin) with the predicted mobility (Offord, Methods Enzym., 47, 51–69 [1977]) of the wanted product. A faint second spot was visible that corresponded to the predicted mobility of the bis-alkylated cysteamine.

The reaction mixture was applied directly to a column of DOWEX 50X8 (3×15 cm) previously equilibrated with pyridine-acetic acid-water, 25:1:225, v/v, pH 6.5). The column was then washed with 200 ml of $H_2O$ followed by 50 ml of the pH 6.5 buffer. The wanted product was liberated from the column with 100 ml of ammonia solution (4M). The ammonia eluate was rotary evaporated for 20 min. and then freeze-dried; yield 493 mg of electrophoretically homogeneous material.

(b) Preparation of des-Ala$^{B30}$-insulin-B29-S-(2.3-dihydroxylpropyl)-cysteamide A sample of the product obtained under (a) (200 mg) was dissolved in 1.118 ml of butane-1,4-diol. Glacial acetic acid (37.5 μl) was added. The pH (glass electrode, very slow response) was raised to 7.0 with approx. 100 μl of a saturated solution of Tris(base) in butane-1,4-diol.

This solution was used to prepare the wanted product in a manner precisely analogous to that described in Example 4 (including the work-up). The protein product had the electrophoretic and ion-exchange properties expected of a mono-amide-substituted insulin, but its principal characterization lay in its use for the Schiffbase-mediated coupling to m-aminobenzoic acid and the detailed study of this latter product (see below).

(c) Coupling of des-Ala$^{B30}$-insulin-B29-S-(2,3-dihydroxylpropyl)-cysteamide to m-aminobenzoic Acid 2 mg of the substituted insulin amide obtained according to (b) above, was dissolved in 150 μl of sodium acetate buffer (0.48 M, pH 5.6, 7 M in urea). To this were added 16 μl of freshly made up periodic acid (4 g/l $H_2O$) and 83 μl of a solution of m-aminobenzoic acid (1.23 M). This latter solution was made by adjusting a 0.1 M solution of the acid to pH 6.5 with strong sodium hydroxide solution, lyophilizing and re-dissolving to 1.23 M. Finally, 16.6 μl of sodium cyanoborohydride (30 mM) was added. After 60 min. the mixture was dialysed and re-dissolved in 1 ml of HCl (0.01 M). This solution was applied for HPLC on a C18 column as described in the preceding Examples and developed with a linear gradient of 29–35% (v/v) acetonitrile in 0.3 M ammonium sulphate, lasting 15 minutes. The stock ammonium sulphate solution (3 M) used to make these eluants had been adjusted to pH 2.7 (glass electrode) with strong $H_2SO_4$. The product peak, corresponding to about 90% of the protein, emerged approx. 2 min. after the position of the starting material. The protein was absorbed from the appropriate pooled fractions onto a SEP PAK cartridge, after blowing off the acetonitrile. After washing the cartridge with 0.1% (v/v) aqueous trifluoroacetic acid/10% (v/v) aqueous acetonitrile, the product was eluted with 2 ml of 0.1% aqueous trifluoroacetic acid/40% aqueous acetonitrile. The protein, recovered by blowing off the acetonitrile and then lyophilizing, was strongly fluorescent. It was characterized by its mobility on cellulose-acetate electrophoresis and by digestion with Armillaria protease. The small fragment from the Armillaria digest was characterised by FAB-MS.

Example 8

General Procedure for the Preparation of IqGs Labelled at the C Termini of Their Chains with DTPA (a) Selection of Optimal Conditions A monoclonal or polyclonal IgG (9 mg/ml, isotonic saline) is mixed with buffer (Na-phosphate, 0.1 M, pH 8.5), p-aminophenyl-alanine-amide (460 mg/ml), and carboxypeptidase Y (2 mg/ml) in the ratio 4.5:5.5:6.5:1 by volume. The mixture is allowed to stand at room temperature. At chosen times after the start of the reaction (normally after 20 min., 60 min., 2.5 h, 5 h, 18 h) samples of 6.5 μl are taken and precipitated with 2 μl of aqueous trichloroacetic acid, 10% (w/v). The precipitate is collected by centrifugation and washed by centrifugation in a further 200 μl of the trichloroacetic acid solution. The pellet is dissolved in saturated aqueous urea, precipitated and washed once more using 10% trichloroacetic acid. (This extensive washing is necessary to eliminate traces of the p-aminophenylalanine amide, since this compound is present at the start at a very high concentration). The pellet is dissolved in acetate buffer (acetic acid, 10%, brought to pH 3.5 with concentrated NaOH) using urea if necessary. It is then treated with 0.5 mg of solid DTPA bis-anhydride under strong agitation. After 2 min., the protein is precipitated and washed again as above. A further cycle of solution, re-precipitation and washing is carried out. The product is then resuspended in 10 μl of the citrate buffer of Example 3 and 1 μl of a solution of $^{111}$In-oxime (Amersham International p.l.c., GB) is added. After 5 minutes, the pellet is collected by centrifugation, washed twice in 200 μl distilled water and counted.

Control samples are prepared in parallel at each time point. These can be obtained from an incubation in which the carboxypeptidase Y solution is replaced by an equivalent volume of distilled water. The optimum time is considered to be when (after correction for the specific radioactivity of the $^{111}$In and subtraction of the background radioactivity indicated by the corresponding control) the radioactivity of the sample corresponds to each IgG molecule having an average of one p-aminophenylalanine-amide-residue at its carboxyl terminus. A representative result, at the specific radioactivity of $^{111}$In used (85 μCi/μmole), is approx. 6000 cpm after subtraction of the control.

(b) Larger-scale Preparation

The x hours incubation, which gave the optimun result in part (a) is then repeated on 0.4 mg IgG. The reaction is stopped by 25-fold dilution to pH 3.5 (10% acetic acid previously adjusted with 5 M aqueous NaOH). The protein is recovered from this mixture by gel filtration (SEPHADEX G-150).

The resulting product is reacted with DTPA-mono-(m-formylanilide) (Example 4) with reduction by cyanoborohydride in the usual way: Protein concentration 4 mg/ml, aldehyde concentration 1 mM, cyanoborohydride concentration 0.75 mM, pH 3.5 (acetate, 1%). After 90 minutes a sample is taken, and labelled by incubation with $^{111}$In as described in, e.g., Example 3. The labelled protein is separated from labelled, un-coupled aldehyde on a SEP PAK cartridge. The aldehyde is removed by 20% aqueous acetonitrile/0.1% aqueous trifluoroacetic acid whilst the protein is not. The radioactivity associated with the protein (after subtraction of appropriate control counts) corresponds to complete reaction. The desired protein is isolated from the remainder of the Schiff-base reaction mixture by gel-filtration, as described before.

Example 9

(a) Preparation of des-Ala$^{B30}$-insulin-B29-N-(formylmethyl)-amid

To 1.33 g of aminoacetaldehyde-diethylacetal (Fluka, Switzerland), were added 8 ml of butane-1,4-diol followed by 450 µl of acetic acid. To 100 mg of des-Ala$^{B30}$-insulin (prepared essentially according to Morihara et al., Biochem. Biophys. Res. Commun. 92, 396 [1980]) were added 3 ml of the acetal solution followed by 0.1 ml of water and the mixture was incubated at 37° C. for 10 min., whereupon the des-Ala$^{B30}$-insulin dissolved. After addition of 100 µl of water containing 10 mg of TPCK-treated trypsin (Worthinton), the solution was incubated at 37° C. for 90 minutes and quenched at 0° C. with an equal volume of pure acetic acid. The resulting solution was diluted with an equal volume of 1% acetic acid then gel filtered on a column (90×2.6 cm) of SEPHADEX G50 (fine grade) eluted with 1% (v/v) acetic acid. The fractions containing the insulin derivative were pooled and lyophilized. The product was further purified by ion-exchange chromatography on an A-25 column as described in Example 4(a). After dialysis against 1% acetic acid and lyophilization, 33 mg product were recovered.

Upon HPLC, the product eluted 1.5 min. later than the des-Ala$^{B30}$-insulin from the C-18 cartridge (conditions as in Example 4(a)), consistent with its being more hydrophobic. Deprotection of the acetal was achieved most conveniently by incubating des-Ala$^{B30}$-insulin-B29-N-(formylmethyl)-amid-diethylacetal (2 mg/ml) in 5% formic acid at 37° C. overnight, under which conditions approximately 90% deprotection was achieved. Upon analytical HPLC, the product, des-Ala$^{B30}$-insulin-B29-N-(formylethyl)-amide, eluted from the C-18 cartridge earlier than the diethylacetal (and very close to the position of des-Ala$^{B30}$-insulin). The des-Ala$^{B30}$-insulin-B29-N-(formylmethyl)-amid was recovered from the dilute formic acid by lyophilization.

(b) Preparation of des-Ala$^{B30}$-insulin-B29-N-(formylmethyl)-amide/m-aminobenzoyl-ferrioxamine B Conjugate To 20 mg des-Ala$^{B30}$-insulin-B29-N-(formylmethyl)-amide dissolved in 0.2 ml of 0.48 M aqueous sodium acetate buffer (pH 5.6) was added 117 mg of m-aminobenzoyl-ferrioxamine B dissolved in 800 µl of dimethylformamide. The pH was adjusted to 5.0 with NaOH and then 500 µl of a 10 mM solution in water of sodium cyanoborohydride (Aldrich) were added. The pH, which had risen to 6.2, was adjusted to 5.5 and the solution was incubated overnight at room temperature. Analytical HPLC on the C-18 cartridge (conditions as in Example 4(a)) showed that about 80% of the starting material had been transformed to a species eluting 3 minutes later than the remaining starting material. This later-eluting species, later identified as the desired product, des-Ala$^{B30}$-insulin-B29-NH—CH$_2$—CH$_2$—NH—C$_6$H$_4$-m-CO-ferrioxamine B, was isolated preparatively on the same column. The product (11.9 mg) was peach-coloured due to the iron present, and was characterized by digestion with trypsin, which yielded des-octapeptide-(B23–B30)-insulin (identified by HPLC and electrophoresis on cellulose acetate at pH 8), the heptapeptide comprising residues B23–B29 (identified by HPLC, by electrophoresis on paper at pH 6.5 and by FAB-MS), and NH$_2$—CH$_2$—CH$_2$—NH—C$_6$H$_4$-m-CO-ferrioxamine B (identified by FAB-MS).

Example 10

(a) Preparation of DTPA-mono-(N-formylmethyl)-amide Diethylacetal

This compound was prepared from DTPA-bisanhydride and aminoacetaldehyde-diethylacetal analogously to the preparation of DTPA-mono-(m-formylanilide) (Example 4(b)), using 20 mg of the amino component and 200 mg of the anhydride. Again, two major products were isolated by HPLC (as in Example 4(b)), 5 mg of a first fraction and 6.1 mg of a second fraction. The first fraction, upon electrophoresis on paper at pH 6.5, had a relative mobility of about −0.76 (Asp=−1.0); it was negative to ninhydrin and was revealed by spraying with DNP-hydrazine in 2 M HCl. Heating to 100° C. was necessary to reveal a yellow spot, suggesting that the acetal protection, much less labile for aliphatic aldehydes than for aromatic ones, was still present. The fraction was characterized as DTPA-mono-(N-formylmethyl)-amide diethylacetal by FAB-MS. The second HPLC fraction was identified by FAB-MS, through strong signals at m/z 624, 646 and 662 (protonated molecular ion, sodium-cationized ion and potassium-cationized ion, respectively), as the dimer resulting from the acylation of two molecules of aminoacetaldehyde by the bisanhydride (DTPA-bis-(n-formylmethyl)-amide-diethylacetal).

(b) Preparation of des-Ala$^{B30}$-insulin-B29-p-amino-L-phenylalanine-methylester/DTPA-mono-(N-formylmethyl)-amide Conjugate The acetal protecting group DTPA-mono-(N-formylmethyl)-amide diethylacetal was removed quantitatively with 1 M HCl. 0.63 mg of deprotected material was dissolved in 250 µl of a buffer made by adjusting the pH of 1% (v/v) aqueous acetic acid to pH 3.5 with 1 M NaOH. 0.2 mg of des-Ala$^{B30}$-insulin-B29-p-amino-L-phenylalanine-methylester see Example 4(a)) was dissolved in 9 µl of the DTPA-mono-(N-formylmethyl)-amide solution and 10 µl of aqueous sodium cyanoborohydride (10 mM) were added. After 90 min. at room temperature, the product, which precipitated, was isolated by acidification (to render it soluble) followed by HPLC on the C-18 cartridge. While the product eluted too close to the position of the starting insulin derivative for any useful separation to be attempted, electrophoresis on cellulose at pH 8 showed that a coupling yield of about 40% had been achieved.

Example 11

Preparation of a Dimer of Insulin Using des-Ala$^{B30}$-insulin-B29-p-amino-L-phenylalanine-methylester and m-benzene-dialdehyde To 100 µl of 1 M propionic acid containing 2 mg des-Ala$^{B30}$-insulin-B29-p-amino-L-phenylalanine-methylester and 26.8 µg of m-benzene-dialdehyde were added 100 µl of 1 M propionic acid containing 62.8 µg sodium cyanoborohydride. After 5 min. at room temperature, the product was isolated by HPLC on a C-18 cartridge. Gel filtration on SEPHADEX G-50 showed that the starting insulin derivative had been transformed, in a yield of about 70%, to a dimeric compound (based on elution from SEPHADEX G-50) which eluted from the C-18 cartridge (analytical run, linear gradient of 25–40%, v/v, acetonitrile in 0.1% trifluoroacetic acid at 1% per min.) appearing three minutes after the starting material. Under similar reaction conditions, unmodified porcine insulin produces less than 1% dimeric material. The structure of the dimeric product is:

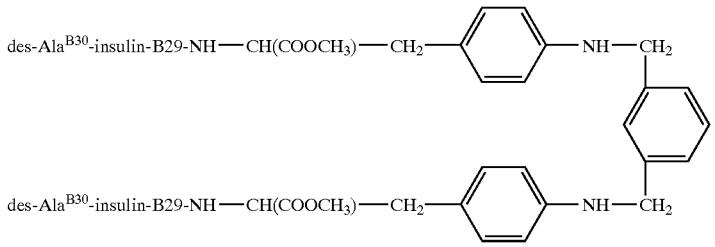

Example 12
Preparation of a des-Ala$^{B30}$-insulin-B29-p-amino-L-phenylalanine/des-Ala$^{B30}$-insulin-B29-m-formylanilide Conjugate 10.2 mg of des-Ala$^{B30}$-insulin-B29-p-amino-L-phenylalanine-methylester (prepared as described in Example 4(a)) was saponified in 5 ml of aqueous 1% (w/v) ammonium bicarbonate solution brought to pH 9.5 with NaOH. After incubation at 37° C. for 24 h, the saponified product was isolated on a Sep-pak according to the manufacturer's instructions, eluting with 50% (v/v) aqueous acetonitrile which was 0.05% in trifluoroacetic acid. Saponification of the methylester was confirmed by electrophoresis on cellulose-acetate at pH 8. The product was recovered by lyophilization after removal of the acetonitrile on the rotary evaporator at room temperature. To one volume of a solution of des-Ala$^{B30}$-insulin-B29-p-amino-L-phenylalanine (50 mg/ml in 1 M propionic acid) was added one volume of a solution of des-Ala$^{B30}$-insulin-B29-m-formylanilide (prepared according to Example 1(a) with purification by HPLC; also 50 mg/ml in 1 M propionic acid) and half a volume of a solution of sodium cyanoborohydride (3.14 mg/ml) in 1 M propionic acid). After 4 min., it was shown by HPLC (C-18 cartridge) that about 70% of the starting protein has been transformed to a more hydrophobic material eluting two minutes later than the starting amine and having the properties of a dimer of presumed structure:

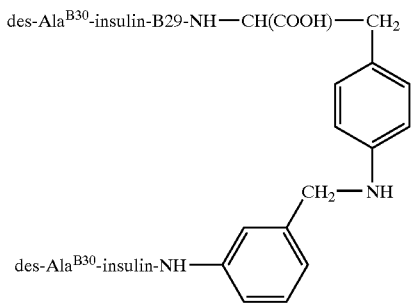

Example 13
(a) Preparation of N-hydroxysuccinimide Ester of 4-methoxy-3-nitrobenzoic Acid 1.97 g (10 mmoles) of 4-methoxy-3-nitrobenzoic acid was dissolved in 50 ml of acetonitrile. 1.15 g (10 mmoles) N-hydroxysuccinimide was added with agitation. Finally 2.063 g (10 mmoles) of N,N'-dicyclohexylcarbodiimide were added and the mixture agitated. After 2 hours at approx. 20° C. a precipitate of dicyclohexyl-urea had formed. The solution was filtered through a Gooch 3G funnel. The formation of ester was determined by t.l.c. of the filtrate (CHCl$_3$/MeOH=9:1, v/v). Observation under U.V. revealed the ester as a dark spot of $R_f$ approx. 0.9. After evaporation of the acetonitrile a whitish-yellow powder remained in the flask. The powder was redissolved in 50 ml of hot isopropanol. Approximately 2 spatula-tips activated charcoal were added and the solution was boiled in a boiling water-bath for about 5 minutes. The boiling solution was quickly poured through a sintered glass filter (G4, previously heated by a passage of hot isopropanol) into a hot flask. The solution was allowed to cool down overnight. White, needle-like crystals were formed (m.p. approx. 145–152° C.) having the expected t.l.c. properties.

(b) Insulin Activation with N-hydroxysuccinimide Ester of 4-methoxy-3-nitrobenzoic Acid 61 mg (10 μmole) of insulin (porcine) were dissolved in 2.1 ml of DMSO. To this were added 900 μl of a solution of N-ethyl-morpholine-carbonate, pH 8.3 (this solution was prepared freshly from 10 ml of N-ethyl-morpholine and powdered dry ice with stirring until pH of the solution, as verified on an electrode, was 8.3).

A solution of 3.6 mg of the N-hydroxysuccinimide ester of 4-methoxy-3-nitrobenzoic acid was made in 100 μl of DMSO. This was added to the above insulin solution with agitation. The reaction mixture was allowed to stand at ambient temperature for 20 minutes. The ratio of N-hydroxysuccinimide ester to insulin was 1:1 on a molar basis. The reaction was stopped by acidification, i.e. addition of 60 μl HCl, 37% (pH of reaction solution approx. 2.5 on paper). The acidified reaction solution was dialysed against NH$_4$HCO$_3$ (1%), then lyophilized.

The nitro-benzoyl-insulin derivative was purified by ion-exchange on a 11×2.5 cm DEAE-A 25 column (flow rate approx. 1 ml/min, equilibrated in 0.1 M tris-HCl/7 M urea, pH 8.4, elution with a 0 to 0.15 M NaCl gradient). The peak fractions were pooled, dialysed first against water then against NH$_4$HCO$_3$ (1%, w/v) and then lyophilized. Each pool was analysed by HPLC (same conditions as before) to confirm the purity of the monosubstituted nitrobenzoyl-insulin.

(c) Reduction of Monosubstituted Nitrobenzoyl-insulin to Monosubstituted Aminobenzoyl-insulin 5 mg of purified monosubstituted-nitrobenzoyl-insulin was dissolved in 1 ml tris-HCl (50 mM) pH 8.3 buffer. 60 μl of a sodium dithionite solution (50 mM in H$_2$O) was added to it (3.6 excess dithionite over insulin). After agitation on a Vortex mixer the solution was allowed to stand at ambient temperature (approx. 20° C.) for 3 minutes.

The reaction was stopped by diluting the solution to 4 ml with 50 mM tris-HCl pH 8.3 buffer. The reaction solution was desalted by passage through a SEP-PAK cartridge (WATERS). The sample was adsorbed onto the cartridge with a solution of 10% $CH_3CN/0.1\%$ TFA and eluted off with a solution of 40% $CH_3CN/0.1\%$ TFA. The excess acetonitrile was dried off under a stream of compressed air, then the solution was lyophilized.

The resultant aminobenzoyl-insulin powder was purified by preparative HPLC (RP-18 column; buffer: 0.3 M $(NH_4)_2SO_4$, pH 2.7; load at 24% $CH_3CN$, linear gradient up to 35% $CH_3CN$ over 45 minutes). The peak fractions were pooled separately, the excess acetonitrile was evaporated under a stream of compressed air and the remaining solutions were then lyophilized.

The peaks that emerged at or near the expected position for aminobenzoyl-substituted insulin were tested as follows. The freeze-dried pool was dissolved to 7.9 mg/ml in 10 nM HCl and trial Schiff-base couplings to benzaldehyde were carried out in the usual way (10 mM, aqueous, solubilised with a little solid urea). The pools which were judged by HPLC to have coupled most effectively with the benzaldehyde solution were selected for subsequent tests. Two peaks, presumably isomers, were seen to couple very well with benzaldehyde.

(d) Preparation of Aminobenzoyl-insulin/des-$Ala^{B30}$-insulin-B29-m-formylanilide Conjugate Method:

The purified insulin-aryl-$NH_2$ (aminobenzoyl-insulin) pool was coupled to insulin-aryl-CHO (des-$Ala^{B30}$-insulin-B29-m-formylanilide, prepared as described in Example 1(a)) using the following method:

| | | |
|---|---|---|
| Insulin-aryl-$NH_2$ | (6.8 mg/ml) | 5 μl (34 μg or 5.7 nmoles) |
| + Insulin-aryl-CHO | (7.8 mg/ml) | 4.3 μl (34 μg or 5.7 nmoles) |
| + $NaBH_3CN$ | (3 mM) | 2 μl (6 nmoles) |
| + Acetic acid 4.17% adjusted to pH 3.5 with strong NaOH | | 1.2 μl |

After vortexing and leaving at ambient temperature for 30 minutes, the solution was analysed by HPLC as before and by a 15–25% SDS gradient gel (at pH 8.3). Both HPLC and the SDS gel showed formation of coupled material. On the gel a band of MW approx, 11,900 was observed confirming the presence of a dimer of insulin. cl Example 14

(a) Preparation of Fab-p-aminophenylalanine Amide with Carboxypeptidase Y

A solution of an Fab antibody fragment was prepared by papain digestion of an antibody, gel-filtration chromatography, and concentration by membrane filtration using standard methods. The solution was 4.3 mg/ml in protein, and the solvent was Dulbecco phosphate-buffered saline. To 70 μl of this solution was added 7 mg of solid p-aminophenylalanine amide, freeze dried from a solution that had been adjusted to pH 8.5 with 0.01M NaOH or 0.01M HCl as necessary. Once the p-amino-phenylalanine amide was in solution, 7 μl of carboxypeptidase Y Carlsberg (1 mg solid corresponding to 0.106 mg protein, per 50 microliters) was added. After two and a half hours at room temperature, the enzyme was inhibited with PMSF (7 microliters of a 10 mg/ml solution in acetonitrile) and left at 0° C. for 10 minutes. The digest was then diluted with 500 microliters of Dulbecco phosphate-buffered saline and subjected to gel filtration (SEPHADEX G50; column 60 cm×0.9 cm diameter). The protein peak was collected and concentrated to 1.1 mg/ml (monitored by $O.D._{280}$; O.D. 1.3=1 mg/ml).

(b) Preparation of Fab-p-aminophenylalanine Amide with Papain

To one volume of a solution of an Fab fragment (the same solution conditions as that used in (a) above) were added two volumes of a solution of 1M p-aminophenylalanine amide (pH adjusted to pH 6.7 with acetic acid). Three volumes of butane-1,4-diol were added, followed by 0.06 volumes of cysteine (1M). A 50:50 mixture of papain suspension and butane-1,4-diol was prepared (final papain content 18 mg/ml) and 0.28 volumes of the mixture were added at once to the Fab solution. The apparent pH was checked with pH paper: if the apparent value was lower than pH 6.2 it was raised to 6.2–6.7 with 0.01M NaOH (with careful, rapid mixing). After 18 hours at room temperature the papain was inactivated by addition of the appropriate volume of iodoacetic acid, 0.5M, brought to pH 7.0 with 1% $NaHCO_3$ solution. After incubation for 10 minutes at room temperature the protein conjugate was isolated on SEPHADEX G50 as described above.

(c) Preparation of Fab-p-aminophenylalanine Amide with Trypsin

To one volume of a solution of an Fab fragment (the same solution conditions as in (a) were added two volumes of the solution of 1M p-aminophenylalanine amide pH 6.7 used in (b). Butane-1,4-diol (3.2 volumes) was then added, followed by 0.2 volumes of bovine trypsin (10 mg/ml in HCl $10^{-2}$M). After 18 hours at room temperature the pH was brought to 3.5 with acetic acid, and the modified Fab isolated by gel filtration as above.

(d) Preparation of $N^\epsilon$-dansyl-$N^\alpha$-(m-formylbenzoyl)-lysine

4—Carbobenzaldehyde (Fluka) was stirred with dry methanol at room temperature for 24 hours. T.l.c. on silica with chloroform/methanol (9:1, v/v) showed essentially quantitative conversion to the acetal, as judged by inspection after spraying with a saturated solution of 2,4-dinitrophenylhydrazine in 2M HCl (Rf of product approx. 0.3, Rf of starting aldehyde approx. 0.15). The product was recovered by rotary evaporation without heating and traces of water were removed from the white cake by the addition of 50 ml dichloromethane followed by rotary evaporation once again. To the cake were added, with mixing, 2.3 g of N-hydroxysuccinimide in 120 ml. ethyl acetate, followed by 4.12 g dicyclohexylcarbodiimide in 20 ml ethylacetate. The quantitative transfer of the carbodiimide from the weighing tube to the reaction vessel was ensured by a wash with 10 ml ethylacetate. A heavy precipitate formed after about 1 minute. After one hour at room temperature, the precipitate was removed by filtration. The precipitate was washed with 20 ml ethylacetate and the combined filtrates were rotary evaporated to an oil, which spontaneously crystallised. Recrystallisation from 120 ml propan-2-ol gave 2.75 g of a white crystalline product. Mass spectrometry (fast-atom bombardment) showed a strong signal at m/z 262, interpreted as $M+H^+$-MeOH. The compound gives a single spot on t.l.c. (the same chromatographic system and spray as above) with an Rf of about 0.6.

$N^\epsilon$-dansyl-L-lysine (Sigma, 9.5 mg) was dissolved in 100 µl dimethylformamide under gentle warming. N-ethylmorpholine (3 µl) was added, so that the apparent pH, as judged by spotting onto moist pH paper, was between 8 and 8.5. This solution was mixed with a solution of 7.3 mg of the hydroxysuccinimido ester of 4-carboxybenzaldehyde dimethylacetal in 50 µl dimethylformamide. The apparent pH was checked in the same way as before, and adjusted with N-ethylmorpholine (1 µl at a time) if necessary. After 4 hours and 30 minutes (the apparent pH having been checked from time to time and adjusted if necessary), a similar solution of 7.3 mg of the active ester was added and the reaction allowed to continue for a further 4 hours. The reaction, as judged by t.l.c., was then essentially complete. The t.l.c. system was that described in Example 1(c) and the Rf values were approx. 0.3 and 0.6 for dansyl-lysine and the product, respectively. The mixture was then diluted to 1 ml with acetic acid (1%, v/v), centrifuged, and the supernatant subjected to HPLC (system of Example 4(c)). The major fluorescent peak eluting on the gradient (around 40% acetonitrile) was pooled, and the acetonitrile was driven off in a current of air. The product was characterized by measurement of its electrophoretic mobility at pH 6.5 (predicted and observed, 0.5 [mAsp=1.0]). To this stock solution (600 µl) were added 6 µl M HCl, and the solution was diluted ten-fold with $10^{-3}$M HCl. This brought the concentration to 0.7 mM, as judged by direct comparison of the u.v. absorption spectrum with that of a solution of dansyl-lysine of known concentration. It was assumed that the optical density of the dansyl chromophore would be approximately the same in the two substances.

It was expected that the acetal protection would be removed during HPLC (pH of the system approx. 2). This hypothesis was confirmed by the fact that the product underwent rapid coupling to aromatic amines via the Schiff-base/cyanohydride reaction without the need for any prior acid treatment.

(e) Coupling between Fab-p-aminophenylalanine Amide and $N^\epsilon$-dansyl-$N^\alpha$-(m-formylbenzoyl)-lysine The Fab derivative obtained in acccordance with procedure (a) (1.1 mg/ml) was buffered at either pH 3.5 (acetate buffer made by adjusting 12% (v/v) acetic acid to pH 3.5 with concentrated NaOH and then diluting to a final equivalent of 10% acetic acid) or pH 2 (1M propionic acid brought down to pH 2 by 1M HCl). In either case 2 volumes of buffer were used for every five volumes of Fab solution. To this solution was added 1 volume of a solution of the lysine derivative obtained in accordance with procedure (d) (approx. 0.7 mM in $10^{-3}$M HCl) and 1 volume of sodium cyanoborohydride (3 mM). In controls, the cyanoborohydride was replaced by water. Samples were withdrawn from time to time and the extent of the coupling reaction was judged by cellulose-acetate electrophoresis. Salt and any uncoupled aldehyde were largely eliminated before running by acetone precipitation of the protein, which was taken up for electrophoresis in the electrophoresis buffer (2% formic acid/8% acetic acid/8M urea). The coupling appeared to reach its maximum between 20 and 80 minutes. The fluorescent protein conjugate was isolated by precipitation (cold acetone) and washing. Controls showed no fluorescence.

Example 15

Preparation of m-aminobenzoyl-polyglutamic Acid Substituted on the Side Chains with Ferrioxamine B Polyglutamic acid (Sigma Inc., glutamic acid polymerised by peptide-bond formation through its alpha amino and carboxyl groups, average number of residues per chain approx. 50) was suspended in dimethylsulphoxide (100 mg in 1 ml DMSO). The apparent pH, as judged externally with damp pH paper, was brought to 8 by cautious addition of N-methyl-morpholine. Hydroxysuccinimido ester of m-aminobenzoic acid (Example 1) was then added (75 mg). The apparent pH was readjusted to 8 with N-methyl-morpholine. The polyglutamic-acid suspension gradually cleared over the course of 18 hours at 20° C. Paper electrophoresis showed that the amino group had essentially fully reacted after 24 hours. Water (5 ml) was then added and the solution allowed to stand for 1 h at 20° C., in order to hydrolyse any remaining active ester (the pH remained above 7 during the period). A precipitate which formed as soon as the water was added was removed at the end of the 1 hour's period by centrifugation. The supernatant was adjusted to 5 with acetic acid (10%, v/v, previously adjusted to pH 3). The solution was stored and worked up as required in lots equivalent to 5–10 mg of polyglutamic acid. The work-up consisted of adsorption on a Sep-Pak $C_{18}$ cartridge (type 51910) that had been equilibrated with HCl, $10^{-4}$M. The wash was with 2×10 ml of the same HCl solution, and desorption with 2 ml $10^{-4}$M HCl/acetonitrile (6:4, v/v). The acetonitrile was then removed in a current of air, and the turbid suspension of the polyglutamic acid derivative was dried under reduced pressure. This material was coupled to ferrioxamine B as follows.

To 1 volume of a solution of the polyglutamic acid derivative (20 mg/ml in dimethylformamide) were added 1.8 volumes of a solution of 1,1-carbonyl-diimidazole (80 mg/ml DMF). After 30 minutes at 20° C. solid ferrioxamine B was added (1 mg/14 µl of reaction mixture). The great majority of the ferrioxamine dissolved at once. After 30 minutes the reaction mixture was diluted with 5 volumes of acetic acid (0.1%, aqueous) and applied to SEPHADEX G50. The polymer peak was concentrated on SEP PAK as described above, except that the equilibration solution was 0.1% aqueous $CF_3COOH$, the wash was 0.1% aqueous $CF_3COOH$/acetonitrile, 19:1 (v/v) and the desorption took place in 0.1% aqueous $CF_3COOH$/acetonitrile, 1:4 (v/v). After removing the acetonitrile from the desorbed fraction in a current of air, the aqueous solution was applied for HPLC ($C_{18}$ reversed-phase) in 0.1% $CF_3COOH$, with a gradient of 0–100% acetonitrile in 30 minutes. The wanted product eluted as a relatively broad peak at around 50% acetonitrile. The peak fractions were dried in the usual way. The BOC protection was removed by anhydrous $CF_3COOH$ (50 µl per mg of product for 30 minutes at 20° C.). Spectroscopy and amino-acid analysis showed an incorporation of between 0.71 and 0.76 residues of ferrioxamine B per residue of glutamic acid.

Example 16

(a) Preparation of the Chelon $H_2N$—O—$CH_2$—CO-ferrioxamine B 1.093 g O-carboxymethyl-hydroxylamine-hemihydrochloride (Fluka) was N-protected by introduction of the tert-butyloxycarbonyl group under standard conditions (water/methanol) using 4.365 g $Boc_2O$ (Fluka). The pH was maintained at 9 with NaOH. After 16 hours at 22° C., the solution was evaporated and the solid residue taken up in 10 ml of water. After cooling to 0° C., the solution was acidified carefully to pH 3 and the precipitate which formed was collected by centrifugation. Yield after drying under high vacuum: 1 g. The product was identified as Boc-NH—O—$CH_2$—COOH by negative ion FAB/MS (intense M–H at m/z 190).

191 mg of Boc-NH—O—CH$_2$—COOH were dissolved in 25 ml DMSO and 115 mg of N-hydroxysuccinimide were added. To the resulting solution were added 210 mg of dicyclohexylcarbodiimide dissolved in 5 ml DMSO and the reaction mixture was left at room temperature overnight. A solution of ferrioxamine B in DMSO (6.6 ml, 15 mg/ml) was added and sufficient N-methyl-morpholine to bring the pH (externally measured with moist Merck pH strip having chemically bound dyes to permit rinsing with water to remove the colour due to ferrioxamine) to 8. After 4 hours at room temperature the reaction mixture was diluted to about 150 ml with water and the N,N'-dicyclohexylurea precipitate removed by centrifugation. The solution was acidified to pH 3 with acetic acid and the product was recovered, in portions, on a C18 Sep-Pak column as follows. After an initial methanol wash, the Sep-Pak column was equilibrated with 0.1% acetic acid, a portion of the sample applied, and the column washed with 0.1% acetic acid to remove DMSO. Washing with 0.1% acetic acid/acetonitrile (9:1, v/v) removed traces of unreacted ferrioxamine B, and the wanted product was eluted with 0.1% acetic acid/acetonitrile (7:3, v/v). After pooling of the product portions, solvent was removed by rotary evaporation and the Boc group removed by dissolving the product in 1 ml trifluoroacetic acid and incubating at 22° C. for 45 minutes. The acid was removed by rotary evaporation, whereupon the residue was taken up in water and purified in a Sep-Pak column as described above, except that this time, since the hydrophobic Boc group had been removed, the colour was eluted with 0.1% acetic acid/acetonitrile (9:1, v/v). Acetonitrile was removed by rotary evaporation and the aqueous solution was then freeze-dried: yield about 35 mg. The product ran as an orange-brown, ninhydrin-negative, single spot on silica t.l.c. in butanol/acetic acid/water/acetone (7:2:4:7, v/v) with an Rf of about 0.35 (Rf ferrioxamine about 0.1), it ran as a single spot a little slower than ferrioxamine on paper electrophoresis at pH 1.9, and was identified as NH$_2$—O—CH$_2$—CO-ferrioxamine B by positive ion FAB/MS (intense M+H at m/z 687).

(b) Coupling of the Chelon H$_2$N—O—CH$_2$—CO-ferrioxamine B to Aldehydes and Ketones In order to show that the new chelon, NH$_2$—O—CH$_2$—CO-ferrioxamine B, reacts under mild conditions with aldehydes and ketones, the chelon (about 5 mM) was incubated respectively with 4-carboxybenzaldehyde (about 1.3 mM), with o-aminobenzaldehyde (about 3 mM), with 3-aminoacetophenone (about 3 mM), with N-acetyl-3-aminoacetophenone (about 3 mM), with 4-aminoacetophenone (about 3 mM), with N-acetyl-4-aminoacetophenone (about 3 mM), with heptanaldehyde (about 3 mM), with nonan-5-one (about 3 mM), and with pyruvate (about 3 mM), in acetate buffer at pH 3, 4, 5, and in pyridine acetate buffer at pH 6.5, at 22° C. Control incubations were performed with ferrioxamine B under similar conditions. With the hydroxylamino chelon, rapid reaction ensued with all reagents at pH 3 and 4, to give a coloured product more hydrophobic than the chelon in the t.l.c. system described above, and in the expected ratio in view of the excess of chelon. The spots did not trail, and no further reaction occured over at least 24 hours. The more reactive reagents (pyruvate and aldehydes except o-aminobenzaldehyde) reacted within 5 hours up to pH 6.5. Under similar conditions, unsubstituted ferrioxamine, which has an aliphatic amino group, showed no sign of reaction with any of the reagents: any products which may have been formed by temporary association of carbonyl compound with ferrioxamine must have been unstable to the conditions of analysis (t.l.c. in butanol/acetic acid/water/acetone). The oximes obtained by the coupling are stable compounds.

(c) Coupling of desAla$^{B30}$-insulin-B29-m-formanilide to H$_2$N—O—CH$_2$—CO-ferrioxamine B 1 mg of desAla$^{B30}$-insulin-B29-m-formanilide (obtained according to Example 1a) was dissolved in 100 μl of a solution of NH$_2$—O—CH$_2$—CO-ferrioxamine B (10 mM in 0.1% acetic acid) and incubated at 22° C. for 2 hours. This led to expected formation of the O-alkyloxime of the protein derivative, which was detected by t.l.c. on silica sheets using butanol/acetic acid/water/acetone (7:2:4:7, v/v), which showed the presence of a coloured spot of almost zero mobility, staining positive with cadmium-ninhydrin. This material was shown to be the expected conjugate, desAla$^{B30}$-insulinyl-3-aminobenzaldehyde-O-alkyloxime, by reversed phase HPLC (using 0.1% TFA and acetonitrile, a Macherey-Nagel 5 μm C8 300 A 4 mm×25 cm column at a flow rate of 1 ml/min; the protein derivative, now coloured, elutes close to the position of desAla$^{B30}$-insulinyl-3-aminobenzaldehyde, but well separated from starting material, on a gradient of 1% acetonitrile per minute) and by electrophoresis on cellulose acetate at pH 8.0 (the coloured protein derivative ran in a position characteristic of insulin derivatives having lost one negative charge, and stained red with Ponceau S).

Example 17

3-Aminopropane-1,2-diol (0.5M) was coupled to desAla$^{B30}$-insulin (4 mM) in 90% butane-1,4-diol at pH 6.5 (uncorrected glass electrode, pH adjusted with acetic acid) within 2 hours at 22° C. using TPCK-treated bovine trypsin (enzyme/substrate ratio 1:10, w/w) as catalyst. The reaction was very clean and the coupling yield as judged by electrophoresis on cellulose acetate was about 70%. A procedure using 1,3-diaminopropane-2-ol (0.5M) in place of 3-aminopropane-1,2-diol gave a similar result.

The desAla$^{B30}$-insulin-B29-derivatives are susceptible to periodate oxidation under mild conditions yielding a derivative with a carboxy terminal aldehyde group.

Example 18

(a) Preparation of desAla$^{B30}$-insulin-B29-m-acetanilide 10 mM desAla$^{B30}$-insulin in 90% butane-1,4-diol was coupled to 3-aminoacetophenone (0.5M) at a pH (uncorrected glass electrode) of 5.5 (pH adjusted with acetic acid) for a time of 5 hours at 22° C. using TPCK-treated bovine trypsin (enzyme/substrate ratio 1:10, w/w) as catalyst. The reaction was very clean as judged by electrophoresis on cellulose acetate and the coupling yield was about 70%. The reaction was quenched with acetic acid and the mixture applied to a column of Sephadex G50 fine (2.6 cm×90 cm), equilibrated and eluted with 1% acetic acid. This step removed trypsin and small molecules, including excess reagent. The insulin peak was lyophilised (yield 8.8 mg) and shown to be a mixture of coupled and uncoupled product (coupled product about 70%) by electrophoresis on cellulose acetate at pH 8.0. Coupled product was separated from uncoupled product by reversed phase HPLC (using 0.1% TFA and acetonitrile, a Macherey-Nagel 5 μm C8 300 A 4 mm×25 cm column at a flow rate of 1 ml/min; the coupled product elutes later, well separated from desAla-insulin on a gradient of 1% acetonitrile/min.

(b) Coupling of desAla$^{B30}$-insulin-B29-m-acetanilide to H$_2$N—O—CH$_2$—CO-ferrioxamine B A portion of the product obtained (0.8 mg) was incubated at room temperature in solution in 100 μl 0.1% acetic acid with 10 mM of NH$_2$—O—CH$_2$—CO-ferrioxamine B. After a few hours, t.l.c. (on silica sheets using butanol/acetic acid/water/acetone, 7:2:4:7, v/v) showed presence of a coloured spot of almost zero mobility, staining positive with cadmium-ninhydrin. This material was shown to be the expected conjugate, desAla$^{B30}$-insulin-B29-m-acetyl-anilide/H$_2$N—O—CH$_2$—CO-ferrioxamine B-oxime by reversed phase HPLC on the same Macherey-Nagel column (the coupled protein derivative, now coloured, elutes close to the position of desAla$^{B30}$-insulin-B29-m-acetanilide) and by electrophoresis on cellulose acetate at pH 8.0 (the coloured protein derivative runs in a position characteristic of insulin derivatives having lost one negative charge, and stains red with Ponceau S).

Example 19

(a) Preparation of Porcine [glyoxyloyl$^{A1}$]insulin and [glyoxyloyl$^{A1}$, benzyloxalyl$^{B1}$]insulin 12 mg of porcine insulin were dissolved in 12 ml of a solution containing 2M pyridine, 0.8M acetic acid, 10 mM sodium glyoxylate and 2 mM CuSO$_4$ (pH 5.5). The reaction was essentially complete after 20 minutes but was allowed to continue for 3 hours. Samples taken subsequent to 20 minutes showed on reversed phase HPLC (same system as in Example 18a) little starting insulin, some material eluting at the position of a mono-transaminated species ([glyoxyloyl$^{A1}$]insulin), and the great majority at the position of a di-transaminated species ([glyoxyloyl$^{A1}$, benzyloxalyl$^{B1}$]insulin). The main reaction mixture was diluted to 50 ml with water and passed through a Waters Sep-Pak column, which was then washed with 20 ml of 0.1% aqueous trifluoracetic acid/acetonitrile (9:1, v/v). The modified insulin was then eluted with 2 ml of 0.1% trifluoracetic acid (aqueous)/acetonitrile (2:3, v/v). The acetonitrile was removed in a current of air and the resulting solution was lyophylized.

(b) Coupling of Porcine [qlyoxyloyl$^{A1}$]insulin and [glyoxyloyl$^{A1}$, benzyloxalyl$^{B1}$]insulin to H$_2$N—O—CH$_2$—CO-ferrioxamine B The material obtained according to (a) was coupled to H$_2$N—O—CH$_2$—CO-ferrioxamine B by the identical method described in Example 18b. HPLC permitted the isolation of two coloured protein derivatives, one eluting near the position of the mono-transaminated insulin, and the other (the majority) eluting near the position of the di-transaminated derivative.

Example 20

Ribonuclease S-protein was isolated from ribonuclease S (Sigma Chemical Co.) by reversed phase HPLC on the Beckman machine using the previously mentioned (Example 18a) Macherey-Nagel column and a gradient of acetonitrile, in 0.1% trifluoroacetic acid: the S-protein elutes later and well-separated from the S-peptide, and the elution positions of both S-peptide and S-protein were verified by running authentic standards (obtained from Sigma). The purified S-protein obtained from 5 mg of ribonuclease S, dissolved in 1.2 mM HCl, was buffered at pH 7 with imidazole and the sample divided into two 5 ml aliquots.

One portion was oxidised with 5 μl of a solution of periodic acid (19.2 mg/ml in water) at 22° C. for 6 minutes. After this time, the reaction was quenched with 1 ml ethane-1,2-diol. The reaction mixture was applied to a SEP PAK C18 cartridge equilibrated with 1.2 mM HCl. After washing with 1.2 mM HCl, the protein fraction was eluted with 3 ml 1.2 mM HCl/acetonitrile (4:6, v/v). To half of the eluate was added 1.5 ml NH$_2$—O—CH$_2$—CO-ferrioxamine B (10 mM in 50 mM sodium acetate, pH 5; after mixing 5.1). The sample was incubated overnight at 22° C. Upon preparative HPLC, a coloured, protein-containing material was eluted from the Macherey Nagel column (under conditions similar to those used to isolate the S-protein) close to the position of S-protein: the material still contained some uncoupled protein. The presence of the ferrioxamine chromophore in the material isolated by HPLC was confirmed by spectrophotometry on a Varian Cary instrument.

What we claim is:

1. A composition containing conjugated derivatized protein or polypeptide molecules, or salts thereof, wherein said conjugated derivatized protein or polypeptide molecules of said composition consist essentially of a compound selected from the formula:

A—X—Z—X'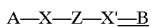B wherein:
A is a protein or polypeptide, and wherein A has a carboxy and amino terminus and is conjugated to X—Z—X'=B only at either said carboxy terminus of A or at said amino terminus of A;
B is a polymeric compound;
X and X' independently from each other are bivalent organic radicals or independently from each other are present or absent;
Z is a bivalent radical selected from the group consisting of:
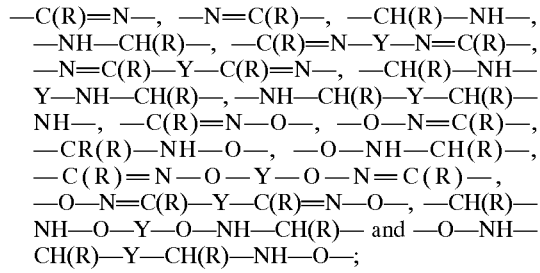
where R is hydrogen or an aliphatic, cycloaliphatic, aromatic or araliphatic hydrocarbon group and
Y is a bivalent organic group;
wherein said conjugated derivatized protein or polypeptide molecules of said composition are produced via formation of a Schiff base, hydrazone, oxime or azomethine compound that results in the presence of at least one radical having the formula —C(R)=N—, or —N=C(R)—, or, when reduced, —CH(R)—NH— or —NH—CH(R)—.

2. The composition of claim 1, wherein said polymeric compound B is a protein or polypeptide that is the same or different from said protein or polypeptide A, or is a reporter group or cytotoxic agent;
and wherein Z is a bivalent radical selected from the group consisting of:
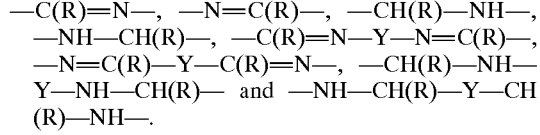

3. The composition of claim 1, wherein said polymeric compound B is a protein or polypeptide that may be the same or different from said protein or polypeptide A, or is a reporter group or cytotoxic agent;

and wherein Z is a bivalent radical selected from the group consisting of:
—C(R)=N—O—, —O—N=C(R)—, —CH(R)—NH—O—, —O—NH—CH(R)—, —C(R)=N—O—Y—O—N=C(R)—, —O—N=C(R)—Y—C(R)=N—O—, —CH(R)—NH—O—Y—O—NH—CH(R)— and —O—NH—CH(R)—Y—CH(R)—NH—O—.

4. The composition of claim 2, wherein R is hydrogen.

5. The composition of claim 3, wherein R is hydrogen.

6. The composition of any of claim 2, 3, 4 or 5, wherein A is connected to —X—Z—X'—B, at the carboxy terminus of A.

7. The composition of any of claim 2, 3, 4 or 5, wherein A is connected to —X—Z—X'—B, at the amino terminus of A.

8. The composition of claim 6, wherein R is hydrogen.

9. The composition of claim 7, wherein R is hydrogen.

10. The composition of any of claim 2 or 4, wherein Z is —C(R)=N—, or —N=C(R)—.

11. The composition of any of claim 3 or 5, wherein Z is —C(R)=N—O— or —O—N=C(R)—.

12. The composition of claim 2, wherein Z is —C(R)=N—, or —N=C(R)—.

13. The composition of claim 12, wherein A is connected to —X—Z—X'—B, at the carboxy terminus of A.

14. The composition of claim 12, wherein A is connected to —X—Z—X'—B, at the amino terminus of A.

15. The composition of claim 13 or 14, wherein R is hydrogen.

16. The composition of claim 2, wherein Z is —C(R)=N—O—, or —O—N=C(R)—.

17. The composition of claim 16, wherein A is connected to —X—Z—X'—B, at the carboxy terminus of A.

18. The composition of claim 16, wherein A is connected to —X—Z—X'—B, at the amino terminus of A.

19. The composition of claim 17 or 18, wherein R is hydrogen.

20. The composition of claim 2, wherein Z is —CH₂—NH—, or —NH—CH₂—.

21. The composition of claim 20, wherein A is connected to —X—Z—X'—B, at the carboxy terminus of A.

22. The composition of claim 20, wherein A is connected to —X—Z—X'—B, at the amino terminus of A.

23. The composition of claim 21 or 22, wherein R is hydrogen.

24. The composition of claim 3, wherein Z is —C(R)=N—O—, or —O—N=C(R)—.

25. The composition of claim 24, wherein A is connected to —X—Z—X'—B, at the carboxy terminus of A.

26. The composition of claim 24, wherein A is connected to —X—Z—X'—B, at the amino terminus of A.

27. The composition of claim 25 or 26, wherein R is hydrogen.

28. The composition of claim 2, wherein Z is —CH=N—Y—N=CH—, —N=CH—Y—CH=N—, —CH2—N—Y—N—CH2—, or —NH—CH2—Y—CH2—NH—.

29. The composition of claim 28, wherein A is connected to —X—Z—X'—B, at the carboxy terminus of A.

30. The composition of claim 28, wherein A is connected to —X—Z—X'—B, at the amino terminus of A.

31. The composition of claim 29 or 30, wherein R is hydrogen.

32. The composition of claim 1, wherein Z is selected from the group consisting of:
—C(R)=N—Y—N=C(R)—, —N=C(R)—Y—C(R)=N—, —CH(R)—NH—Y—NH—CH(R)—, and —NH—CH(R)—Y—CH(R)—NH—;

and at least one of X, X' or Y comprises an aromatic group directly adjacent to an N atom of Z.

33. The composition of claim 32, wherein Y is a phenylene radical.

34. The composition of claim 32, wherein X is a phenylene radical.

35. The composition of claim 32, wherein X' is a phenylene radical.

36. The composition of claim 1, wherein said protein or polypeptide A is conjugated to X—Z—X'—B only at said carboxy terminus of A, wherein said derivatized protein or polypeptide is prepared using reverse proteolysis to attach an aldehyde, aldehyde precursor, or hydrazide to said carboxy terminus followed by said formation of a Schiff base, hydrazone, oxime or azomethine compound.

37. The composition of claim 1, wherein said protein or polypeptide A is conjugated to X—Z—X'—B only at said carboxy terminus of A, wherein X comprises a reactive amino group and wherein said derivatized protein or polypeptide or salt thereof is prepared through a reaction in which said reactive amino group is directly attached to an aromatic group, to the oxygen of an O-alkylated hydroxylamine, or to the nitrogen of the —NH—CO— moiety of a hydrazide.

38. The composition of claim 1, wherein said protein or polypeptide or salt is conjugated exclusively at its amino terminus with the same or a different protein or polypeptide, wherein R is hydrogen.

39. The composition of claim 1, wherein said protein or polypeptide A is an immunoglobulin or a fragment thereof that functions as an immunoglobulin.

40. The composition of claim 39, wherein said immunoglobulin is an IgG molecule or a fragment thereof that functions as an immunoglobulin.

41. The composition of claim 39, wherein said protein or polypeptide is a Fab or F(ab')₂ fragment of an immunoglobulin.

42. A composition containing conjugated derivative protein or polypeptide molecules, or salts thereof, wherein said conjugated derivatized protein or polypeptide molecules of said composition consist essentially of a compound selected from the formula:

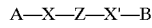

wherein:

A is a protein or polypeptide, and wherein A has a carboxy and amino terminus and is conjugated to X—Z—X' only at either said carboxy terminus of A or at said amino terminus of A;

B is a polymeric compound;

X and X' independently from each other are bivalent organic radicals or independently from each other are present or absent;

Z is a bivalent radical selected from the group consisting of:
—C(R)=N—, —N=C(R)—, —CH(R)—NH—, —NH—CH(R)—, —C(R)=N—Y—N=C(R)—, —N=C(R)—Y—C(R)=N—, —CH(R)—NH—Y—NH—CH(R)—, —NH—CH(R)—Y—CH(R)—NH—, —C(R)=N—O—, —O—N=C(R)—, —CH(R)—NH—O—, —O—NH—CH(R)—, —C(R)═N—O—Y—O—N═C(R)—,
—O—N═C(R)—Y—C(R)═N—O—, —CH(R)—
NH—O—Y—O—NH—CH(R)— and —O—NH—
CH(R)—Y—CH(R)—NH—O—;

where R is hydrogen or an aliphatic, cycloaliphatic, aromatic or araliphatic hydrocarbon group and Y is a bivalent organic group;

wherein said conjugated derivatized protein or polypeptide molecules of said composition are produced via formation of a Schiff base, hydrazone, oxime or azomethine compound that results in the presence of at least one radical having the formula —C(R)═N—, or —N═C(R)—, or, when reduced, —CH(R)—NH— or —NH—CH(R)—; and wherein said modified protein or polypeptide or salt thereof is prepared by a process that employs a reaction selected from the group consisting of: reverse proteolysis, transamination, periodate oxidation and a combination or sub-combination thereof.

43. The composition of any of claim 1, 2, 3 or 42, wherein said polymeric compound B is a protein or polypeptide that is the same or different from said protein or polypeptide A, or is a reporter group or cytotoxic agent.

44. The composition of claim 43, wherein said polymeric compound B is a reporter group comprising a metal chelating organic compound.

45. The composition of claim 43, wherein said polymeric compound comprises a compound selected from the group consisting of:

(i) desferioxamine B, or a metal derivative thereof;
(ii) diethylenetriaminepentaacetic acid, or a metal derivative thereof;
(iii) [Nε-(diethylenetriaminepentaacetic acid-alanyl)-Lys]$_5$, or a metal derivative thereof; and
(iv) a polyglutamic acid having at least two ferioxamine B residues coupled thereto.

46. The composition claim 45, wherein said reporter group is [Nε-(diethylenetriaminepentaacetic acid-alanyl)-Lys]$_5$ or a metal derivative thereof.

47. A composition containing modified protein or polypeptide molecules, or salts thereof, wherein said modified protein or polypeptide molecules of said composition consist essentially of a compound selected from the formula:

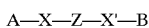
A—X—Z—X'—B wherein:

A is a residue of a protein or polypeptide having a carboxy and amino terminus and is connected to X—Z—X'—B exclusively at said carboxy or amino terminus;

B is a polymeric compound;

X and X' independently from each other are bivalent organic radicals or independently from each other are present or absent;

Z is a bivalent radical selected from the group consisting of:
—C(R)═N—, —N═C(R)—, —CH(R)—NH—,
—NH—CH(R)—, —C(R)═N—Y—N═C(R)—,
—N═C(R)—Y—C(R)═N—, —CH(R)—NH—
Y—NH—CH(R)—, —NH—CH(R)—Y—CH(R)—
NH—, —C(R)═N—O—, —O—N═C(R)—,
—CH(R)—NH—O—, —O—NH—CH(R)—,
—C(R)═N—O—Y—O—N═C(R)—,
—O—N═C(R)—Y—C(R)═N—O—, —CH(R)—
NH—O—Y—O—NH—CH(R)— and —O—NH—
CH(R)—Y—CH(R)—NH—O—; where R is hydrogen or an aliphatic, cycloaliphatic, aromatic or araliphatic hydrocarbon group; and Y is a bivalent organic group; said modified protein or polypeptide being produced by a method comprising condensing a compound of the formula:

A—X—R$^1$ wherein R$^1$ is a —CO—R group, an acetalized formyl group, or an amino or protected amino group, and A, R, and X are as defined above, with a compound of formula:

R$^2$—X'—B or a compound of formula:

R$^2$—Y—R$^2$ where R$^2$ is amino when R$^1$ is —CO—R or acetalized formyl and R2 is —CO—R or acetalized formyl when R$^1$ is amino, and X', Y, R and B are as defined above, to form a Schiff base, hydrazone, oxime or azomethine compound, and optionally, reducing the —C(R)═N— or —N═C(R) formed by the condensation to CH(R)—NH— or —NH—CH(R)—, respectively, and optionally forming a salt.

48. The composition of claim 47, wherein said polymeric compound B is a protein or polypeptide that is the same or different from said protein or polypeptide A, or is a reporter group or cytotoxic agent.

49. The composition of claim 48, wherein said polymeric compound B is a reporter group comprising a metal chelating organic compound.

50. A composition containing conjugated protein or polypeptide derivatives, wherein said conjugated protein or polypeptide derivatives of said composition have a C-terminus and an N-terminus and consist essentially of a compound selected from the group consisting of (1) a protein or polypeptide that is connected only at said C-terminus to a reporter group through a Schiff-base radical of the formula —C(R)═N— or —N═C(R)—, or, when reduced, a radical of the formula —CH(R)—NH— or —NH—C(R)—, and (2) a protein or polypeptide that is connected only at said N-terminus to a reporter group through a Schiff-base radical of the formula —C(R)═N— or —N═C(R)—, or, when reduced, a radical of the formula —CH(R)—NH— or —NH—C(R)—, where R is hydrogen or an aliphatic, cycloaliphatic, aromatic or araliphatic hydrocarbon group.

51. The composition of claim 50, wherein said conjugated protein or polypeptide derivatives of said composition consist essentially of protein or polypeptide derivatives that are conjugated exclusively at their C-terminus to said reporter group.

52. The composition of claim 50, wherein said conjugated protein or polypeptide derivatives of said composition consist essentially of protein or polypeptide derivatives that are conjugated exclusively at their N-terminus to said reporter group.

53. The composition of claim 51 or 52, wherein said reporter group is selected from the group consisting of a metal chelator and polymeric compound.

54. The composition of claim 53, wherein said reporter group comprises a polymeric compound.

55. The composition of claim 54, wherein said polymeric compound comprises a protein or polypeptide.

56. A composition containing conjugated protein or polypeptide derivatives, wherein said conjugated protein or polypeptide derivatives of said composition have a C-terminus and an N-terminus and consist essentially of a compound selected from the group consisting of (1) a protein or polypeptide that is connected only at said C-terminus to a polymeric compound through a Schiff-base radical of the formula —C(R)=N— or —N=C(R)—, or, when reduced, a radical of the formula —CH(R)—NH— or —NH—C(R)—, and (2) a protein or polypeptide that is connected only at said N-terminus to a polymeric compound through a Schiff-base radical of the formula —C(R)=N— or —N=C(R)—, or, when reduced, a radical of the formula —CH(R)—NH— or —NH—C(R)—, where R is hydrogen or an aliphatic, cycloaliphatic, aromatic or araliphatic hydrocarbon group.

57. The composition of claim 56, wherein said protein or polypeptide derivatives of said composition consist essentially of protein or polypeptide derivatives that are conjugated exclusively at their C-terminus to said polymeric compound.

58. The composition of claim 56, wherein said protein or polypeptide derivatives of said composition consist essentially of protein or polypeptide derivatives that are conjugated exclusively at their N-terminus to said polymeric compound.

59. The composition of claim 56 or 57, wherein said polymeric compound comprises a reporter group.

60. The composition of claim 56 or 57, wherein said polymeric compound comprises a protein or polypeptide.

61. A composition containing conjugated protein or polypeptide derivatives, wherein said conjugated protein or polypeptide derivatives of said composition have a C-terminus and an N-terminus and consist essentially of a compound selected from the group consisting of (1) a protein or polypeptide that is connected only at said C-terminus to a cytotoxic agent through a Schiff-base radical of the formula —C(R)=N— or —N=C(R)—, or, when reduced, radical of the formula —CH(R)—NH— or —NH—C(R)—, and (2) a protein or polypeptide that is connected only at said N-terminus to a cytotoxic agent through a Schiff-base radical of the formula —C(R)=N— or —N=C(R)—, or, when reduced, a radical of the formula —CH(R)—NH— or —NH—C(R)—, where R is hydrogen or an aliphatic, cycloaliphatic, aromatic or araliphatic hydrocarbon group.

62. The composition of claim 61, wherein said protein or polypeptide derivatives of said composition consist essentially of protein or polypeptide derivatives that are conjugated exclusively at their C-terminus to said cytotoxic agent.

63. The composition of claim 61, wherein said protein or polypeptide derivatives of said composition consist essentially of protein or polypeptide derivatives that are conjugated exclusively at their N-terminus to said cytotoxic agent.

64. A composition containing conjugated protein or polypeptide derivatives, wherein said conjugated protein or polypeptide derivatives of said composition have a C-terminus and an N-terminus and consist essentially of a compound selected from the group consisting of (1) a protein or polypeptide that is connected only at said C-terminus to a polymeric conjugation reagent via a Schiff-base radical of the formula —C(R)=N— or —N=C(R)—, or, when reduced, a radical of the formula —CH(R)—NH— or —NH—C(R)—, and (2) a protein or polypeptide that is connected only at said N-terminus to a polymeric conjugation reagent through a Schiff-base radical of the formula —C(R)=NH= or —NH—C(R)—, or, when reduced, a radical of the formula —CH(R)—NH— or —NH—C(R)—, where R is hydrogen or an aliphatic, cycloaliphatic, aromatic or araliphatic hydrocarbon group, said protein or polypeptide derivative being produced by condensation of complementary reactive moieties comprising a first reactant having a moiety selected from the group consisting of a reactive aldehyde, acetalized aldehyde and ketone, and a second reactant having a reactive amino group, wherein at least one of said reactants is a protein or polypeptide having a C- or N-terminus comprising said aldehyde, acetalized aldehyde, ketone or amino group.

65. The composition of claim 64, wherein said protein or polypeptide derivatives of said composition consist essentially of protein or polypeptide derivatives that are conjugated exclusively at their C-terminus to said conjugation reagent.

66. The composition of claim 64, wherein said protein or polypeptide derivatives of said composition consist essentially of protein or polypeptide derivatives that are conjugated exclusively at their N-terminus to said conjugation reagent.

67. The composition of any of claim 65 or 66, wherein said conjugation reagent comprises a reporter group.

68. The composition of any of claim 65 or 66, wherein said conjugation reagent comprises a protein or polypeptide.

69. The composition of any of claim 65 or 66, wherein said conjugation reagent comprises a cytotoxic agent.

* * * * *